(12) United States Patent
Lavallee et al.

(10) Patent No.: US 12,396,691 B2
(45) Date of Patent: Aug. 26, 2025

(54) X-RAY IMAGING SYSTEM

(71) Applicant: ECENTIAL ROBOTICS, Gieres (FR)

(72) Inventors: Stéphane Lavallee, Saint Martin d'Uriage (FR); David Armand, Saint Egreve France (FR); Denis Ropp, Ugine (FR); Vincent Ledier, Saint Theoffrey (FR)

(73) Assignee: ECENTIAL ROBOTICS, Gieres (FR)

( * ) Notice: Subject to any disclaimer, the term of this patent is extended or adjusted under 35 U.S.C. 154(b) by 277 days.

(21) Appl. No.: 18/030,619

(22) PCT Filed: Oct. 7, 2021

(86) PCT No.: PCT/EP2021/077639
§ 371 (c)(1),
(2) Date: Apr. 6, 2023

(87) PCT Pub. No.: WO2022/074092
PCT Pub. Date: Apr. 14, 2022

(65) Prior Publication Data
US 2024/0000406 A1    Jan. 4, 2024

(30) Foreign Application Priority Data
Oct. 7, 2020 (EP) .................................... 20306169

(51) Int. Cl.
*A61B 6/00* (2024.01)
*B25J 13/08* (2006.01)

(52) U.S. Cl.
CPC .......... *A61B 6/4405* (2013.01); *A61B 6/4441* (2013.01); *A61B 6/4476* (2013.01); *A61B 6/547* (2013.01); *B25J 13/085* (2013.01)

(58) Field of Classification Search
CPC ... A61B 6/4405; A61B 6/4441; A61B 6/4458; A61B 6/4476; A61B 6/547
See application file for complete search history.

(56) References Cited

U.S. PATENT DOCUMENTS

| | | |
|---|---|---|
| 6,213,638 B1 | 4/2001 | Rattner |
| 2005/0151498 A1 | 7/2005 | Bauer |
| 2008/0013692 A1* | 1/2008 | Maschke .................. B25J 11/00 378/198 |
| 2010/0239073 A1* | 9/2010 | Eaves .................. A61B 6/4441 378/198 |
| 2016/0082596 A1 | 3/2016 | Barth |
| 2020/0069377 A1 | 3/2020 | Finley |

OTHER PUBLICATIONS

PCT Search Report in related PCT Application No. PCT/EP2021/077639, mailed Jan. 14, 2022.
European Search Report in related EP Application No. 20306169 mailed Mar. 23, 2021.

* cited by examiner

*Primary Examiner* — Dani Fox
(74) *Attorney, Agent, or Firm* — Thomas | Horstemeyer, LLP

(57) ABSTRACT

The invention relates to an X-ray imaging system comprising a mobile base (10), a motorized arm (20), and a C-arm (30) adapted to be mounted on the mobile base (10) by means of the motorized arm (20), wherein the C-arm (30) comprises an X-ray source (31) and an X-ray detector (32), wherein the motorized arm (20) presents at least three rotation axes (Z1, Z2, Z3) directed along a substantially common vertical direction (Z).

19 Claims, 12 Drawing Sheets

X-RAY IMAGING SYSTEM

CROSS REFERENCE TO RELATED APPLICATIONS

This application is the 35 U.S.C. § 371 national stage application of PCT Application No. PCT/EP2021/077639, filed Oct. 7, 2021, which application claims the benefit of European Application No. EP 20306169.2 filed Oct. 7, 2020, both of which are hereby incorporated by reference herein in their entireties.

The present invention relates to an X-ray imaging system comprising a C-arm adapted to be moved by a motorized arm.

GENERAL TECHNICAL FIELD AND PRIOR ART

Mobile X-ray imaging systems are frequently used during medical procedures and surgical interventions, in order to acquire 2D or 3D X-ray images. The acquired images may be used to provide physicians with information about the anatomical situation of the person and/or the position and orientation of surgical instruments during surgery.

X-ray imaging systems may be used in the context of a surgical intervention carried out onto a person's bone, for example for implantation of orthopedic implants such as pedicular screws in the spine, implantation of various orthopedic implants in bones, or reduction and fixation of fractures during traumatological procedures, or insertion of catheters or stents during cardio-vascular or urology procedures. X-ray imaging systems may also be used in the context of positioning guides or canulae at desired positions with respect to one or several predefined regions of interest.

The X-ray imaging system may be coupled to other surgical systems, such as a surgical motorized system, a localization system, etc. The X-ray images acquired by the X-ray imaging system may be used to control these other surgical systems.

Conventional X-ray imaging systems use X-rays to produce two-dimensional (2D) images of a region of interest to be imaged. However, 2D images provide limited information. Therefore, three-dimensional (3D) imaging techniques have been developed.

For example, computer tomography is a class of stationary X-ray imaging system used for 3D reconstruction. Tomography reconstruction algorithms, such as cone-beam reconstruction techniques, may be used to reconstruct a 3D image from an imaging dataset comprising multiple 2D images of a region of interest acquired by 2D X-ray detectors. However, computer tomography devices are generally not available in an operating room.

An X-ray imaging system used to acquire such multiple 2D images may comprise a C-arm.

Known C-arm devices that can produce 2D or 3D images are disclosed for example in documents U.S. Pat. No. 7,927,014 B2, DE 10 2016 204 618 A1, US 2020/0121267 A1, and U.S. Pat. No. 9,737,235 B2.

A C-arm presents, in a manner known per se, a C-shaped structure, that is to say a structure substantially shaped as a semicircle. An X-ray source, or X-ray generator, and an X-ray detector, or image detector, are mounted on the C-arm.

The X-ray source and the X-ray detector are mounted on the two opposite semicircle ends of the C-arm, so as to face each other. In order to perform an X-ray imaging, a person must be positioned between the two opposite ends of the C-arms, thus between the X-ray source and the X-ray detector.

The C-arm is mounted on a base via mechanical connections which allow some degrees of freedom. Indeed, the C-arm has to be moved in different positions and orientations around and along a table on which the person lies, so as to acquire the images required to perform the X-ray imaging.

More particularly, the C-arm may first be positioned away from the base, in order to reach the table on which the person lies, so that the person is positioned between the X-ray source and X-ray detector. Then, the C-arm may be rotated, in a movement called an orbital rotation, around an axis of rotation approximately perpendicular to a plane formed by the C-arm. The C-arm may simultaneously or successively be translated along the table, or perpendicularly to the table, and/or rotated around different axes of rotation.

The mechanical complexity required to give the C-arm the several degrees of freedom which are necessary for X-ray imaging is high.

In order to provide a C-arm capable of enough mobility, known X-ray imaging systems include a motorized arm on which the C-arm is mounted, and which moves the C-arm in the required positions and orientations. The motorized arm is mounted on the base.

However, the C-arm has a consequent weight of around 100 kg, and the number of positions and orientations necessary to perform the X-ray imaging is high. Consequently, the motorized arm is heavy, complex and massive. The motorized arm is therefore costly, and requires a lot of space in the room where the imaging is performed in order to move the C-arm. In particular, in order to move the C-arm in orbital rotation, the motorized arm must extend significantly, which requires complex mechanism and a large available empty space.

Furthermore, the movement of the motorized arm, therefore the position of the C-arm, cannot be controlled with absolute accuracy. The position of the C-arm is thus susceptible to deviate from the commanded position. Thus, the exact relative position of a region of interest relative to a previous region of interest cannot be deduced from the commanded movement of the C-arm. When several separate regions of interest must be acquired, the position of the C-arm must therefore be recalibrated for each region of interest to acquire. Additional recalibration means, such as a recalibration algorithm, are then necessary. This is the case for example when the X-ray imaging requires imaging successively a region of interest corresponding to a foot and then a region of interest corresponding to a knee or a hip, or requires imaging successively several regions of interest corresponding to several different vertebrae.

One possible solution to overcome this problem is the use of a base fixed to the ground. In this case, it cannot be located too close to the table, otherwise the base may hinder the doctor performing the X-ray imaging in certain positions of the system. This further contributes to the complexity, weight and space needed by the imaging system, as the C-arm must be positioned significantly away from the base in order to reach the table.

One other possible solution to overcome this problem is the use of holonomic drive systems, such as described in documents EP 3,646,792 A1 or US 2020/0129251 A1. But a drawback of this solution is that it is not adapted to displacements on long distances, such as from the X-ray imaging system storage room to the operating room. Moreover, holonomic drive systems cannot be operated manually, notably in case of power outage.

GENERAL PRESENTATION OF THE INVENTION

A general aim of the invention is to propose an improved 2D and 3D X-ray imaging system, with an enhanced mobility without the drawbacks of the state of the art.

Another aim of the invention is to propose a mobile X-ray imaging system comprising a motorized arm which is simpler and smaller than conventional motorized arms, while allowing a wide range of positions and orientations of the C-arm.

Another aim of the invention is to provide an X-ray imaging system providing an increased accuracy of the motorized arm displacements. According to a first aspect, the invention is directed towards an X-ray imaging system comprising a mobile base, a motorized arm, and a C-arm adapted to be mounted on the mobile base by means of the motorized arm, wherein the C-arm comprises an X-ray source and an X-ray detector, wherein the motorized arm presents at least three rotation axes directed along a substantially common vertical direction.

Some preferred but not limiting features of the X-ray imaging system described above are the following, taken individually or in combination:

the motorized arm further presents a translation axis in the vertical direction;

the motorized arm further presents at least one additional rotation axis;

the motorized arm further presents at least two additional rotation axes;

the motorized arm presents a kinematic chain of six axes, starting from the mobile base and comprising successively:
  a translation axis along the vertical direction,
  three successive rotation axes parallel to the vertical direction,
  a transverse rotation axis substantially orthogonal to the vertical direction,
  a C-arm rotation axis substantially orthogonal to the vertical direction and to the transverse rotation axis;

the X-ray imaging system further comprises a toppling risk detection unit adapted to estimate a toppling risk of the X-ray imaging system;

the toppling risk detection unit is configured to continuously estimate a toppling risk of the X-ray imaging system based on encoders position of each axis of the motorized arm and a geometric model of the X-ray imaging system including a mass distribution of the X-ray imaging system;

the X-ray imaging system further comprises stabilization means adapted to stabilize the X-ray imaging system;

the stabilization means include mobile counterweights;

the stabilization means include retractable stabilization means adapted to be moved between a retracted position and a deployed position;

in the deployed position, the retractable stabilization means extend at least partially outwardly from the mobile base;

a displacement of the retractable stabilization means between the retracted position and the deployed position include a translation of the retractable stabilization means along a stabilization direction, wherein said translation is substantially proportional to a distance between the proximal end and the distal end of the motorized arm in the stabilization direction;

the retractable stabilization means include at least one retractable suction pad, wherein the at least one retractable suction pad is adapted to adhere to the ground in the deployed position;

the X-ray imaging system further comprises alerting means adapted to alert an operator to move the stabilization means when the toppling risk detection unit detects a toppling risk;

the motorized arm is further adapted to uncouple the C-arm from the mobile base when the toppling risk detection unit detects a toppling risk greater than a predetermined threshold;

the mobile base comprises motorization means adapted to move the mobile base in a substantially horizontal plane and base position determining means adapted to determine a position of the mobile base in said horizontal plane;

the X-ray imaging system further comprises a control unit adapted to control an actuation of the mobile base and/or the motorized arm;

the toppling risk detection unit is adapted to determine an authorized area of motion of the C-arm according to toppling parameters, and wherein the control unit is adapted to restrict a movement of the motorized arm so as to keep the C-arm within said determined authorized area of motion;

the toppling parameters include operating parameters of the stabilization means;

the X-ray imaging system further comprises a user interface adapted to allow a user to control a movement of the mobile base and/or the motorized arm;

the X-ray imaging system further comprises a sensor adapted to measure a force and/or torque applied by a user on the motorized arm and/or the C-arm, wherein the control unit comprises a cooperative mode, wherein in the cooperative mode, the control unit is adapted to control a movement of the motorized arm in response to the force and/or torque detected by the sensor;

said cooperative mode is parameterized so that:
  when the sensor detects a force and/or torque in one or several direction(s), the control unit applies a substantially proportional force and/or torque to the motorized arm, and
  when the sensor detects a force and/or torque in one or several other direction(s), the control unit does not apply a force and/or torque to the motorized arm;

the X-ray imaging system is adapted to be actuated towards a parking configuration optimized to reduce a footprint of said X-ray imaging system;

the X-ray imaging system further comprises a battery-powered supply unit for safe operation in the case of a power outage;

the battery-powered supply unit is dimensioned so as the X-ray imaging system can return to the parking configuration on said battery.

According to a second aspect, the invention is direction towards a method for acquiring an imaging dataset with an X-ray imaging system according to the first aspect, comprising the following steps:

S1: controlling a movement of the mobile base and/or the motorized arm in order to position the C-arm relative to a predetermined region of interest;

S2: acquiring an imaging dataset of the predetermined region of interest by the X-ray imaging system.

Some preferred but not limiting features of the method for acquiring an imaging dataset described above are the following, taken individually or in combination:

the method further comprises the following steps, performed successively for at least one additional region(s) of interest, after acquiring the imaging dataset of the predetermined region of interest in step S2:

S3: controlling a movement of the mobile base and/or the motorized arm in order to position the C-arm relative to an additional region of interest;

S4: estimating a displacement of the motorized arm corresponding to the movement controlled in step S3 by a motorized arm kinematic model;

S5: acquiring an additional imaging dataset of the additional region of interest by the X-ray imaging system;

S6: estimating a displacement of the X-ray detector of the C-arm between the acquisition of the previous region of interest and the additional region of interest based on the displacement of the motorized arm estimated in step S4;

the steps S3, S4, S5 and S6 are repeated successively for at least two additional regions of interest, wherein the predetermined region of interest is a knee of a person, a first additional region of interest is a hip of the person, and a second additional region of interest is an ankle of the person;

at least two regions of interest among the predetermined region of interest and the at least one additional region(s) of interest are two different sections of a spine of a person;

the method further comprises performing the following steps before each acquisition of an imaging dataset of a region of interest:

S11: positioning a reference tracker in a fixed relation relative to the region of interest to acquire;

S12: estimating a position of the X-ray detector of the C-arm relative to the reference tracker;

and wherein the method further comprises a step S7 of registering the at least one additional region(s) of interest with the predetermined region of interest based on the displacement of the motorized arm estimated in step S4;

the method further comprises the following steps, performed substantially simultaneously:

S7: moving the mobile base;

S8: determining a displacement of the mobile base by base position determining means;

S9: synchronizing a movement of the motorized arm with the displacement of the mobile base determined in step S8 by base motorization means, so that a position of the C-arm remains substantially the same;

the method further comprises a step S110 of controlling, in a coordinated manner, a movement of the motorized arm around at least two of the at least three rotation axes, so as to move the C-arm in a substantially horizontal plane attached to the mobile base;

the method further comprises a step S120 of controlling, in a coordinated manner, a movement of the motorized arm around at least two of the at least three rotation axes, so as to move the C-arm around a fixed point or a fixed axis;

the fixed point or fixed axis is located substantially at an isocenter of the C-arm, at a substantially equal distance from the X-ray source and the X-ray detector;

the method further comprises a step S130 of memorizing, by a control unit, at least one position of the C-arm along with corresponding position parameters of the motorized arm;

the method further comprises a step S140 of controlling a movement of the motorized arm in order to position the C-arm to a position memorized by the control unit.

PRESENTATION OF THE FIGURES

Other features and advantages of the invention will emerge from the following description, which is purely illustrative and non-limiting and must be considered with respect to the appended figures in which.

DESCRIPTION OF SEVERAL EMBODIMENTS

Figure 1:
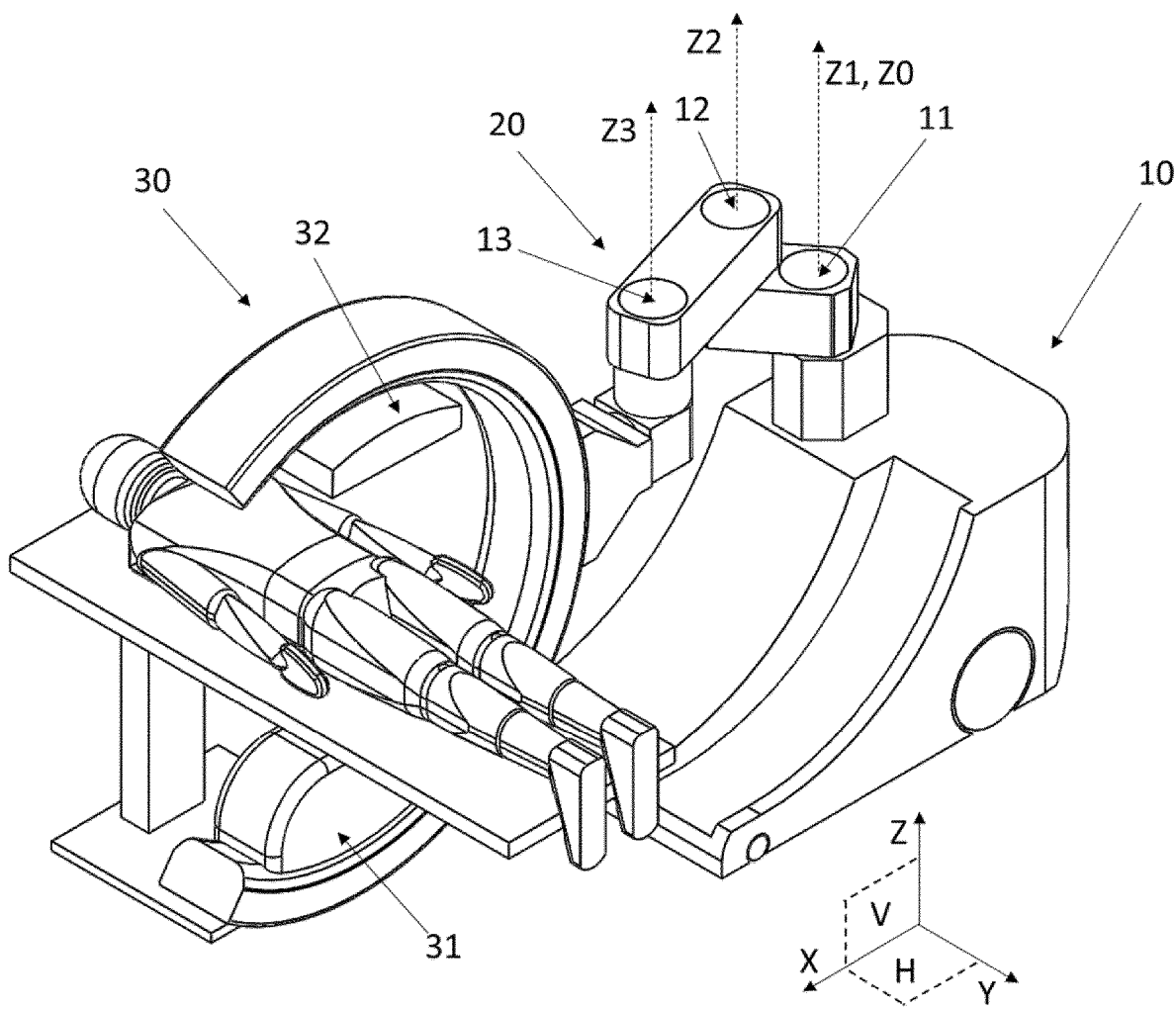
FIG. 1 is a perspective view of an X-ray imaging system according to an embodiment of the invention, the X-ray imaging system being positioned relative to a patient.

General Presentation of an X-Ray Imaging System

Examples of an X-ray imaging system according to different embodiments of the invention are illustrated in FIGS. 1 to 6b.

The X-ray imaging system comprises a mobile base 10, a motorized arm 20, and a C-arm 30 adapted to be mounted on the mobile base 10 by means of the motorized arm 20.

The C-arm 30 comprises an X-ray source 31 and an X-ray detector 32.

The motorized arm 20 presents at least three rotation axes Z1, Z2, Z3 directed along a substantially common vertical direction Z. An example of such three rotation axes Z1, Z2, Z3 is illustrated in the example embodiment of FIG. 1.

A region of interest corresponds to a volume to be acquired by an X-ray imaging technique.

An imaging dataset comprises at least one 2D image or projection of a region of interest acquired by the X-ray imaging device, and/or at least one 3D image of a region of interest. The at least one 3D image of the region of interest may be determined from the at least one 2D image acquired by the X-ray imaging system using tomography techniques.

A horizontal plane H is a plane normal to the vertical direction Z. The horizontal plane H is defined by a longitudinal direction Y and a transverse direction X orthogonal to the longitudinal direction Y.

A table on which a person to be imaged lies may extend in a substantially horizontal plane H. The longitudinal direction Y extends in a direction of a length of the table. The transverse direction X extends in a direction of a width of the table. A ground of the room in which the X-ray imaging is performed may extend in the horizontal plane H.

A vertical plane V corresponds to a plane defined by the vertical direction Z and the transverse direction X.

The movement of the C-arm 30 is managed by means of a single motorized arm 20, and is therefore simple.

The three rotation axes Z1, Z2, Z3 directed along a substantially common vertical direction Z are substantially parallel and articulate different segments of the motorized arm 20 relative to each other, so as to allow the motorized arm 20 to access quickly a wide range of positions in a wide variety of directions. The X-ray imaging system thus allows complex trajectories to be followed, which enables imaging of a large variety of regions of interests, under a large variety of constraints.

More particularly, the motorized arm 20 may move the C-arm 30 by a rotation or a combination of rotations of different segments of the motorized arm 20 around one or several of the three rotation axes Z1, Z2, Z3 of the motorized arm 20.

The motorized arm 20 may for example move the C-arm 30 in the horizontal plane H substantially normal to the vertical direction Z, for example in translation in the transverse direction X, the longitudinal direction Y, or any combination of directions comprised in the horizontal plane H.

A motorized arm 20 comprising three substantially parallel rotation axes Z1, Z2, Z3 also allows a high level of precision of the movement of the motorized arm 20, and therefore an accurate positioning and orienting of the C-arm 30.

The X-ray imaging system thus makes it possible to successively acquire distant imaging datasets of distant regions of interest, by moving the C-arm 30 between the successive acquisitions, while knowing that the movement command has been respected. The effective position of the C-arm 30 substantially corresponds to the commanded position of the C-arm Thus, the position of the X-ray source 31 and of the X-ray detector 32 are known for each successive acquisition of an imaging dataset.

Therefore, when several successive imaging datasets of several separate regions of interest must be acquired, the relative position of the acquired images of the next region of interest relative to the acquired images of the previous region of interest can accurately be deduced from the commanded movement of the C-arm 30. Therefore, the position of the C-arm 30 does not have to be recalibrated by specific recalibration means for the acquired images of different regions of interest.

The C-arm 30 may be positioned successively at different regions of interest, for example a foot, a knee, a hip, several vertebrae, etc. The C-arm 30 successively performs X-ray imaging acquisitions at each of the several regions of interest, in order to acquire several imaging datasets corresponding to each of the several regions of interest. The position of the C-arm 30 may be deduced at any time from the commanded movement of the motorized arm 20, as the command is known to have been respected.

In one example, in an imaging for a scoliosis-related surgical procedure, the X-ray imaging system may have to acquire several imaging datasets of a spine of the person. Each imaging dataset is used to reconstruct a 3D image of a portion of the spine, and each 3D image may be registered with the others without necessitating cumbersome instruments of tedious workflow.

In another example such as a knee or hip surgery, the X-ray imaging system may have to acquire a first imaging dataset of a hip of the person, a second imaging dataset of a knee of the person, and a third imaging dataset of an ankle of the person. Each imaging dataset may be registered with the others.

Finally, the base 10 is a mobile base 10. Therefore, the base 10 may be moved according to the region of interest to acquire, and may be moved in order to cooperate with a movement of the motorized arm 20. The mobile base 10 may be moved between successive acquisitions of different regions of interest. For example, the mobile base 10 may be positioned as close as possible to the region of interest to be acquired without hindering the doctor performing the X-ray imaging. This further reduces the complexity, weight and space needed by the X-ray imaging system.

This solution thus offers a greater flexibility in the acquisitions of imaging datasets with no loss of accuracy and with no significant impact on the weight and cost of the X-ray imaging system.

C-Arm 30

In the following, the term C-arm 30 has a broad signification, and is used to designate an imaging system including a curved segment. More specifically, the term C-arm 30 may refer for example to an imaging gantry presenting a C-shaped structure, or an O-shaped structure.

The C-arm 30 may present a C-shaped structure, that is to say a structure substantially shaped as a semicircle, ending with two opposite ends. Embodiments of such a C-arm 30 with a C-shaped structure are illustrated by way of a non-limiting example in FIGS. 1 to 4b.

The C-shaped structure of the C-arm 30 may be substantially planar. The C-arm 30, more particularly the C-shaped structure of the C-arm 30, may be made of carbon.

The X-ray source 31, or X-ray generator, and the X-ray detector 32, or image detector, may be mounted on the C-shaped structure of the C-arm 30. Each of the X-ray source 31 and the X-ray detector 32 may be mounted next to a respective one of the two opposite ends of the C-arm 30. Thus, the X-ray source 31 and the X-ray detector 32 face each other. When the C-arm 30 is positioned around a table on which a person lies, the person is positioned substantially between the X-ray source 31 and the X-ray detector 32.

The C-shaped structure of the C-arm 30 may extend substantially in a C-arm plane.

Figure 2A:
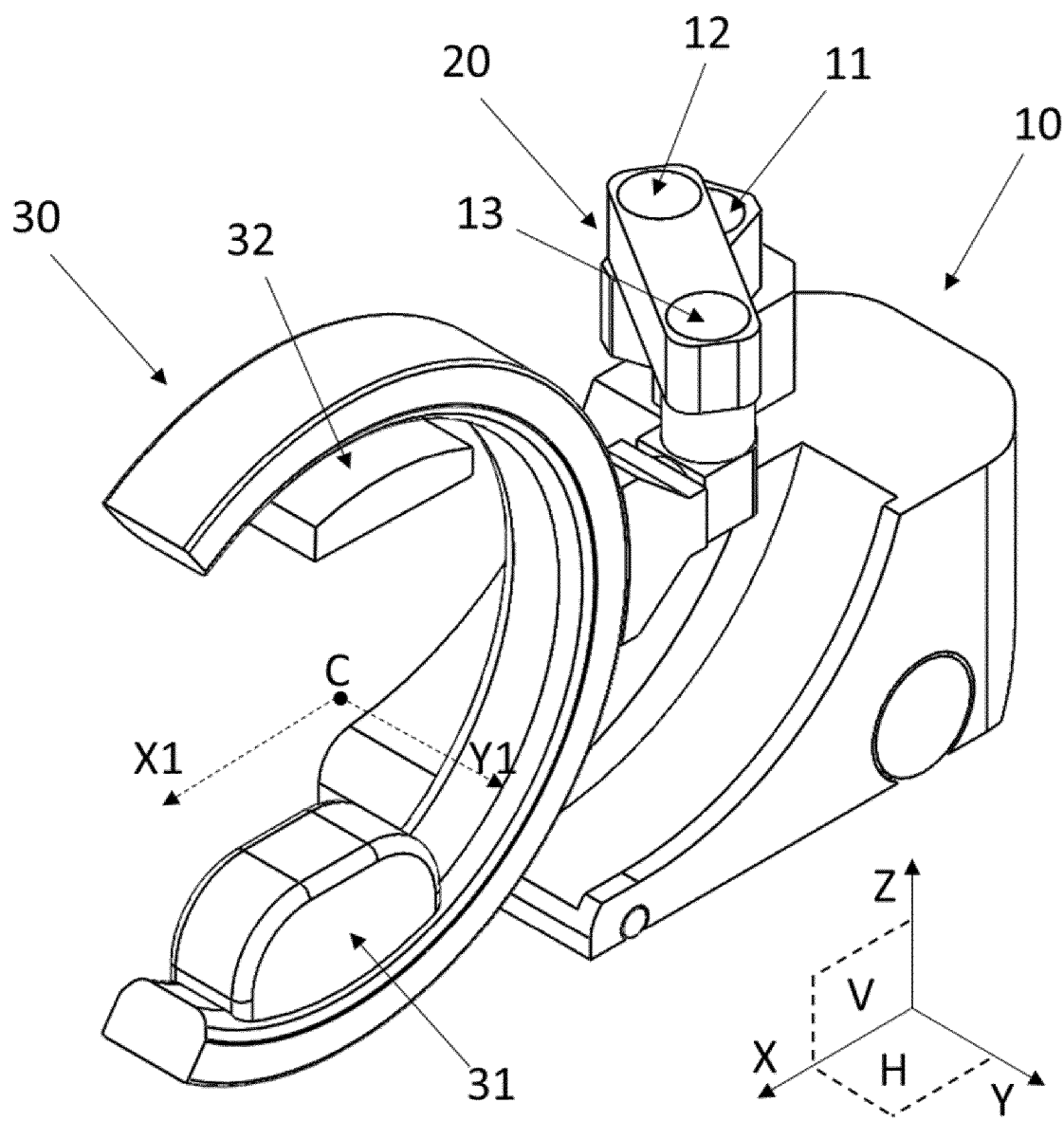
FIG. 2a is a perspective view of an X-ray imaging system according to an embodiment of the invention, with retracted stabilization means.
Figure 2B:
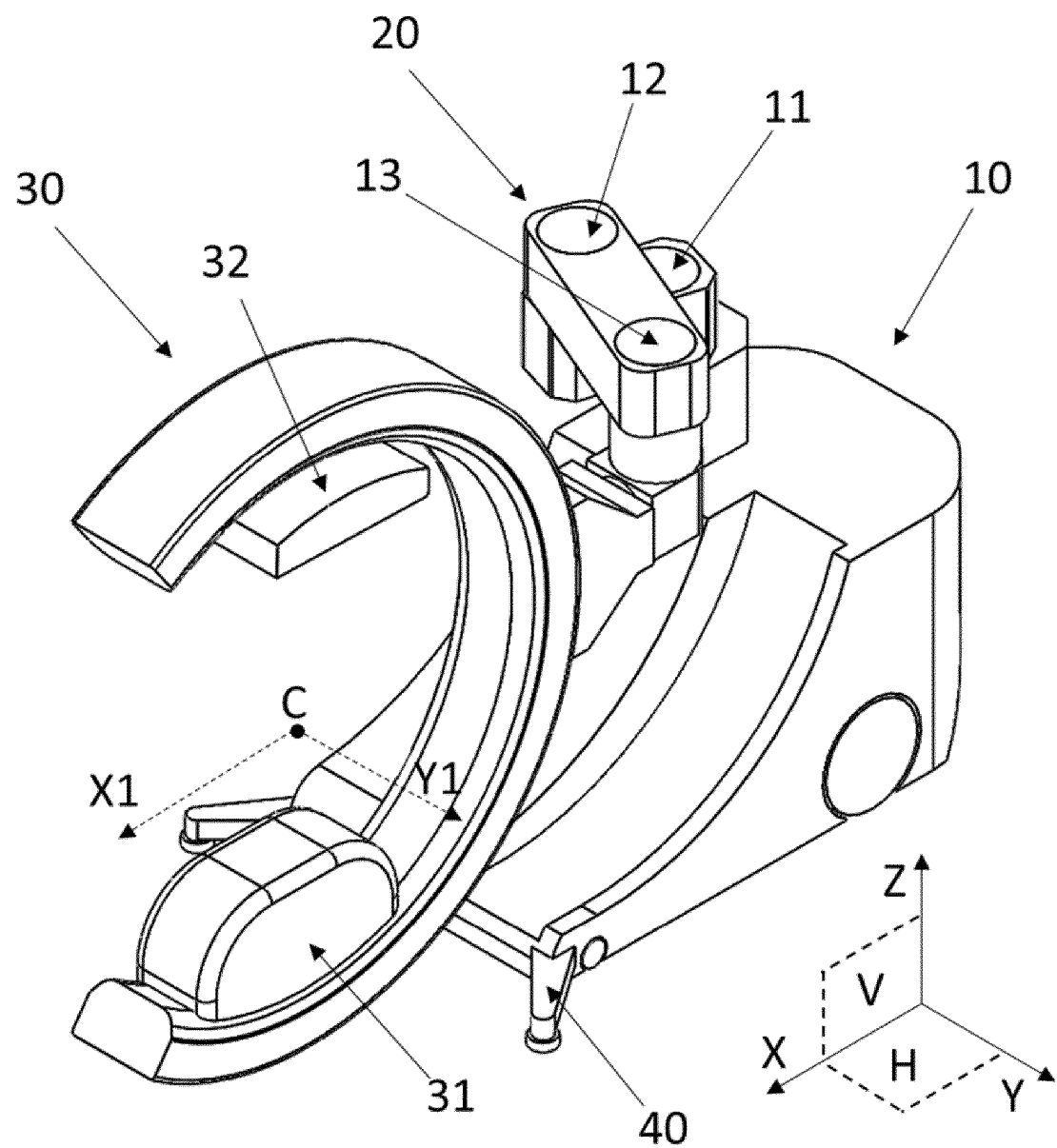
FIG. 2b is a perspective view of the X-ray imaging system illustrated in FIG. 2a, with deployed stabilization means.
Figure 3A:
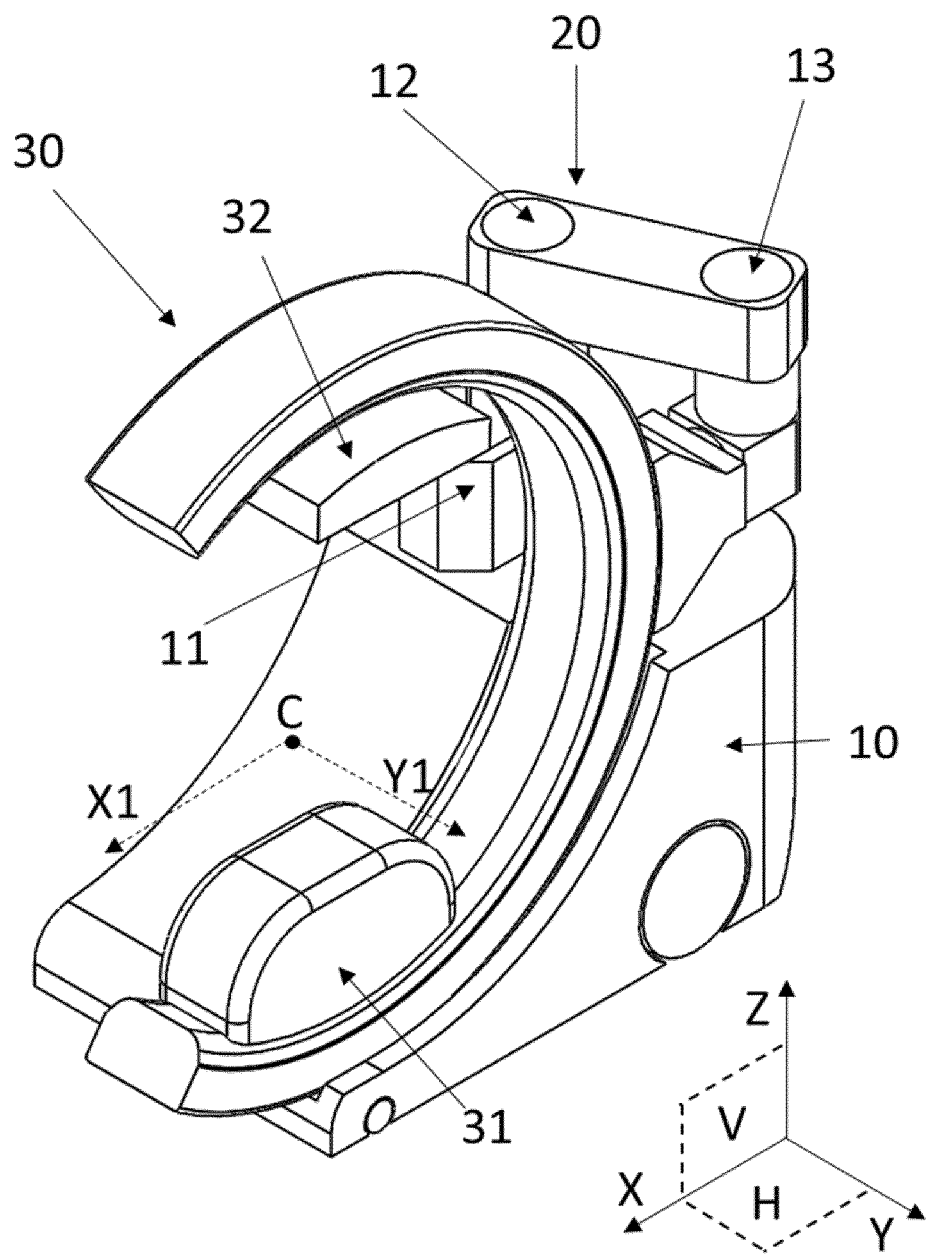
FIGS. 3a to 3c are respectively a perspective view, a side view and a front view of an X-ray imaging system according to an embodiment of the invention, the X-ray imaging system being in the parking configuration.
Figure 3B:
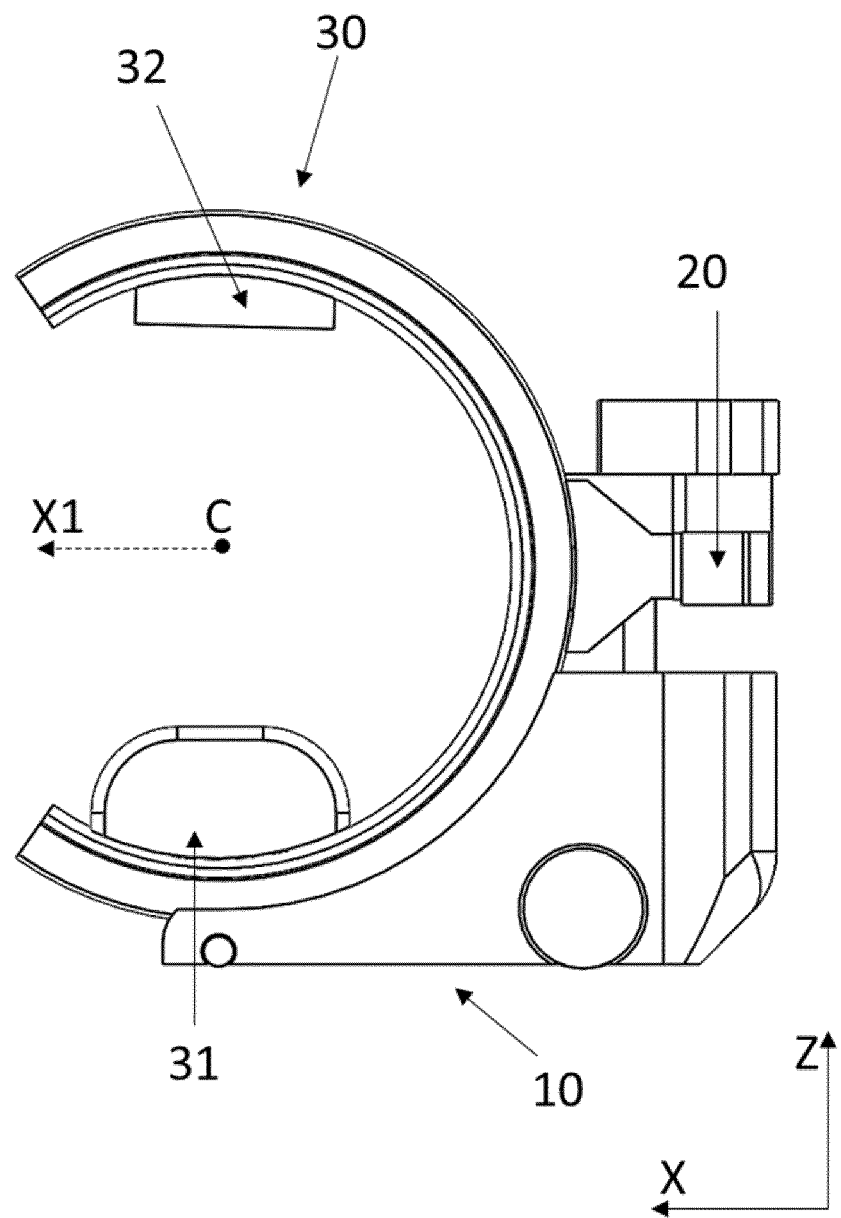
Figure 3C:
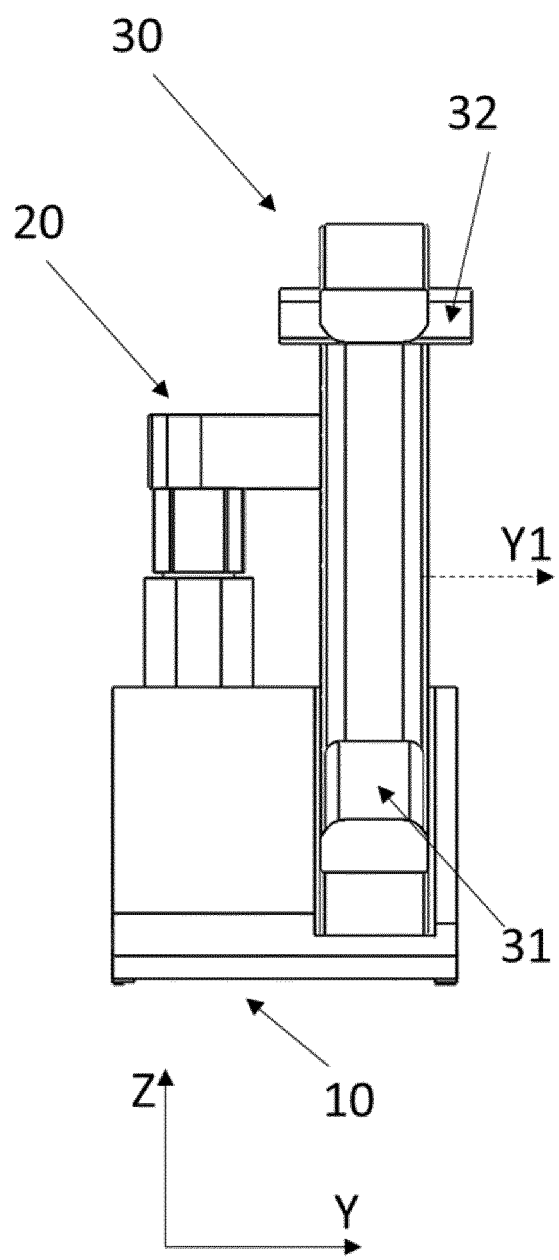

The C-arm 30 may comprise an isocenter C corresponding substantially to a center of the semicircular C-shaped structure of the C-arm 30. The isocenter C of the C-arm 30 is comprised in the C-arm plane. The isocenter C may substantially correspond to a middle of a portion connecting the X-ray source 31 and the X-ray detector 32. FIG. 2a illustrates an example of an isocenter C of a C-arm 30 with a C-shaped structure.

A rotation of the C-arm 30 around the transverse rotation axis X1 is characterized by an angle alpha. The angle alpha corresponds to an angle formed between the C-arm plane and the vertical plane V.

In a nominal position of the C-arm 30, the C-arm plane corresponds to the vertical plane V. The angle alpha is equal to 0°.

When the angle alpha is not equal to zero, that is to say when the C-arm 30 is rotated around the transverse rotation axis X1 relative to the nominal position, the C-arm plane is inclined respective to the vertical plane V defined by the transverse direction X and the vertical direction Z.

The C-arm 30 may present an O-shaped structure. Embodiments of such a C-arm 30 with an O-shaped structure are illustrated by way of a non-limiting example in FIGS. 5a to 6b.

A C-arm 30 with an O-shaped structure may be similar to a C-arm 30 with a C-shaped structure, except that the semicircle of the C-shaped structure is closed so as to form a full ring. A radius of curvature of a C-arm 30 may be substantially the same whether the C-arm 30 has a C-shaped structure or an O-shaped structure.

Figure 6A:
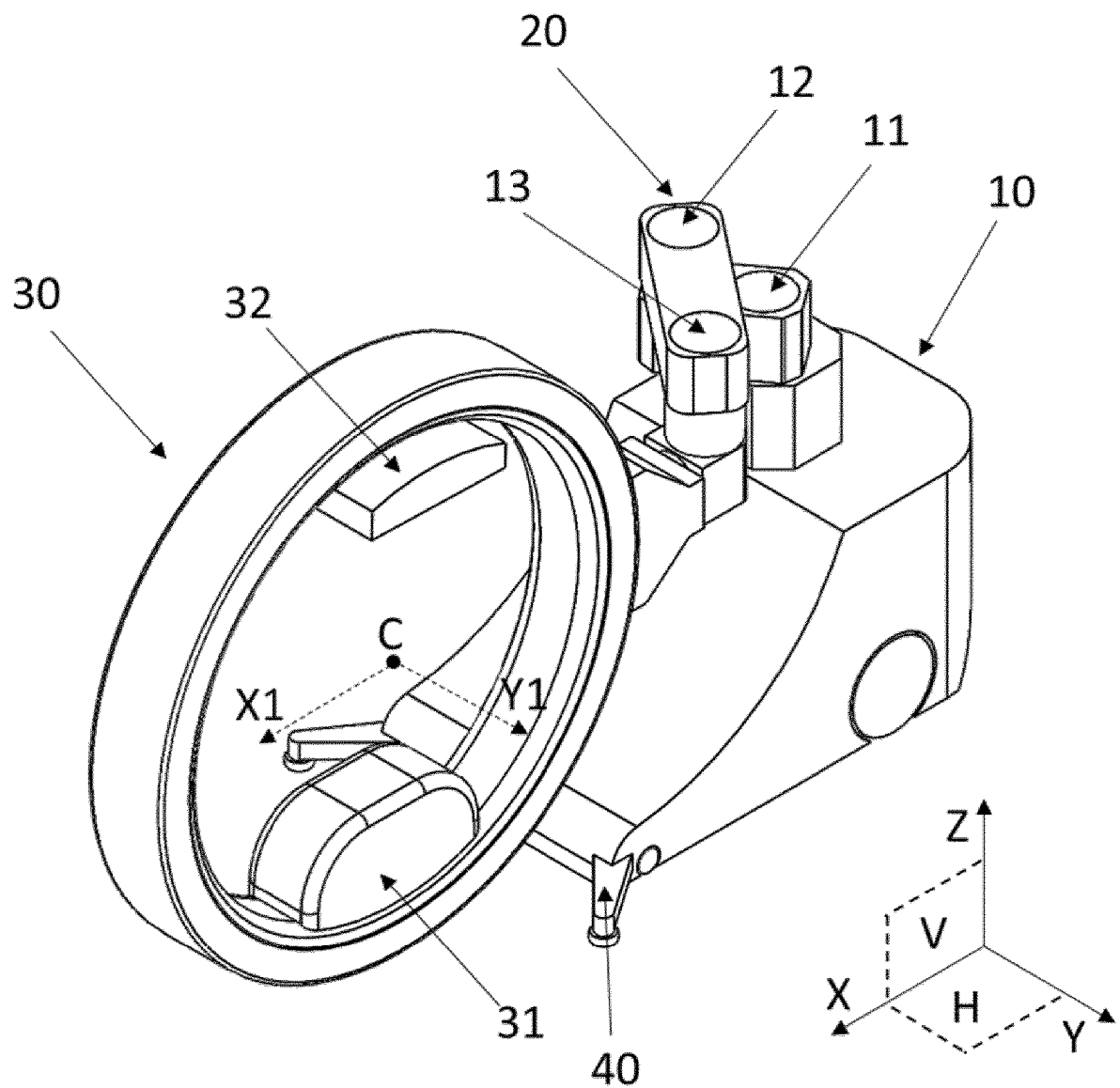
FIG. 6a is a perspective view of an X-ray imaging system according to an embodiment of the invention, the X-ray imaging system having a C-arm with an O-shaped structure and having a symmetrical architecture, with deployed stabilization means.

The isocenter C of the C-arm 30 may correspond substantially to a center of the circle of the O-shaped structure. FIG. 6a illustrates an example of an isocenter C of a C-arm 30 with an O-shaped structure.

Motorized Arm 20

The C-arm 30 is mounted on the motorized arm 20. The motorized arm 20 is mounted on the mobile base 10. The motorized arm 20 may comprise a proximal end adapted to be mounted on the mobile base 10, and a distal end on which the C-arm 30 is adapted to be mounted.

The motorized arm 20 may be a robotic arm of the SCARA (Selective Compliance Articulated Robot Arm) type.

Each rotation axis Z1, Z2, Z3 of the motorized arm 20 may correspond to a respective pivot connection 11, 12, 13. The motorized arm 20 may thus comprise three pivot connections 11, 12, 13 directed along the substantially common vertical direction Z, each pivot connection 11, 12, 13 establishing a respective rotation axis Z1, Z2, Z3. Such parallel-axis pivot connections 11, 12, 13 provide a motorized arm 20 which is rigid in the vertical direction Z, but is slightly compliant in the other directions.

The motorized arm 20 may further present a translation axis Z0 in the vertical direction Z, an example of the translation axis Z0 being illustrated in the example embodiment illustrated in FIG. 1.

The motorized arm 20 is therefore a poly-articulated motorized arm 20, allowing translation of a segment of the motorized arm 20 in the vertical direction Z relative to another segment of the motorized arm 20.

The poly-articulated motorized arm 20 may move the C-arm 30 in translation along the vertical direction Z, that is to say adjusts a position along the vertical direction Z of the C-arm 30 relative to the mobile base 10 and/or table on which the person lies. The motorized arm 20 is thus adapted to move the C-arm 30 upwardly or downwardly relative to the region of interest to be imaged.

This feature is particularly important when the X-ray acquisition necessitates to move the C-arm 30 according to complex trajectories, in particular for 3D acquisition. This feature also allows the X-ray imaging system to adapt to varying positions of operating tables in the vertical direction Z.

The translation axis Z0 may coincide with one of the three rotation axes Z1, Z2, Z3 of the C-arm 30.

The translation axis Z0 in the vertical direction Z of the motorized arm 20 may be achieved by way of a slide connection directed along the vertical direction Z. More particularly, at least one of the pivot connections 11, 12, 13 of the motorized arm 20 may also be a slide connection configured to allow a translation along the vertical direction Z.

The motorized arm 20 may further present at least one additional rotation axis X1, Y1. FIGS. 2a and 6a illustrate in a non-limiting manner two additional rotation axes X1, Y1 of different embodiments of X-ray imaging systems. Each additional rotation axis X1, Y1 of the motorized arm 20 may correspond to a respective additional pivot connection.

The additional rotation axis X1, Y1 may correspond to a C-arm rotation axis Y1. The C-arm rotation axis Y1 may be directed in the longitudinal direction Y and pass through the isocenter C of the C-arm 30. Thus, the motorized arm 20 may change an orientation of the C-arm 30 around the C-arm rotation axis Y1, that is to say may control an orbital rotation of the C-arm 30.

The additional rotation axis X1, Y1 may correspond to a transverse rotation axis X1.

Therefore, the motorized arm 20 may change an orientation of the C-arm 30 relative to the vertical plane V, that is to say may change the angle alpha of the C-arm 30. Thus, the C-arm 30 may be tilted by an angle alpha, which may be constant or variable, relative to the vertical plane V.

Therefore, the X-ray imaging system allows even more complex trajectories to be followed, thus allows imaging of an even larger variety of regions of interests, such as a shoulder, under an even larger variety of constraints. More particularly, the X-ray imaging system allows trajectories involving translation in the horizontal plane H, simultaneously with alpha angle relative to the vertical plane V, while maintaining the isocenter C of the C-arm 30 in a desired position relative to the region of interest.

At least one of the pivot connections 11, 12, 13 of the motorized arm 20 may allow both a rotation around a substantially vertical rotation axis Z1, Z2, Z3 and a rotation around the additional rotation axis X1, Y1.

The motorized arm 20 may further present at least two additional rotation axes X1, Y1. One of the at least two additional rotation axes X1, Y1 may be a C-arm rotation axis Y1, and another of the at least two additional rotation axes X1, Y1 may be a transverse rotation axis X1.

Mobile Base 10

The mobile base 10 may be positioned as close as possible to the region of interest to be acquired, in particular in the transverse direction X, so as to minimize a distance between the base 10 and the C-arm 30, and/or in the longitudinal direction Y. Thus, the lever arm resulting from the combination of the weight of the C-arm 30 and of the motorized arm 20 and their distance to the mobile base 10 is minimized, and the stabilization of the X-ray imaging system is facilitated.

The mobile base 10 may be positioned at an offset relative to the region of interest to be acquired. For example, the base 10 may be moved so as to be spaced apart from the region of interest in the longitudinal direction Y. The movement of the motorized arm 20 may compensate the position of the base 10 so as to maintain the C-arm 30 on the region of interest during movement of the mobile base 10.

Therefore, the X-ray imaging system may continue acquiring an imaging dataset of the region of interest, as the C-arm 30 is maintained in an optimal position for imaging the region of interest, while freeing up space next to the region of interest. Thus, the user may access easily to the region of interest during the acquisition or between two acquisitions of the same region of interest, without being hindered by the X-ray imaging system.

The mobile base 10 may comprise a trolley with wheels so as to be slidable in every direction on the ground of the room in which the X-ray imaging is performed, the ground extending substantially in the horizontal plane H.

The mobile base 10 may comprise front wheels and rear wheels, the front wheels being closest to the motorized arm 20. The front and/or rear wheels may include a pair of spaced apart side wheels, the side wheels being spaced apart in the longitudinal direction Y.

Said front wheels and rear wheels may be of different sizes. Especially, the rear wheels may be of a greater dimension than the front wheels, so as to ensure a greater stability to the X-ray imaging system while the C-arm is moving.

The mobile base 10 may comprise motorization means adapted to move the mobile base 10 in a substantially horizontal plane H, that is to say to move the mobile base 10 in translation on the ground.

The mobile base 10 may comprise base position determining means adapted to determine a position of the mobile base 10 in said horizontal plane H.

The base position determining means may comprise a base position sensor adapted to determine a displacement of the mobile base 10 in the horizontal plane H base 10 on the determination of the position of the mobile base 10 in the horizontal plane H.

The base position determining means may comprise a base position tracker positioned on the mobile base 10. The base position tracker may be adapted to be detected by a camera, and localized according to the images acquired by the camera and showing the base position tracker.

The mobile base 10 may comprise base motorization means adapted to automatically move the base 10.

Kinematic Chain of the Motorized Arm 20

The motorized arm 20 may present a kinematic chain of six axes Z0, Z1, Z2, Z3, X1, Y1, starting from the mobile base 10 and comprising successively:
- a translation axis Z0 along the vertical direction Z,
- three successive rotation axes Z1, Z2, Z3 parallel to the vertical direction Z,
- a transverse rotation axis X1 substantially orthogonal to the vertical direction Z,
- a C-arm rotation axis Y1 substantially orthogonal to the vertical direction Z and to the transverse rotation axis X1.

The three successive rotation axes Z1, Z2, Z3 of the motorized arm may correspond to a proximal rotation axis Z1, an intermediate rotation axis Z2, and a distal rotation axis Z3. When the motorized arm 20 is in a fully extended position, that is to say when the distance between the proximal end and the distal end of the motorized arm 20 is maximal, the proximal rotation axis Z1 is located closest to the base 10, the distal rotation axis Z3 is located closest to the C-arm 30, and the intermediate rotation axis Z2 is located between the proximal rotation axis Z1 and the distal rotation axis Z3.

The proximal end of the motorized arm 20 may be mounted on the base 10 by means of the proximal rotation axis Z1. The C-arm 30 may be mounted on the distal end of the motorized arm 20 by means of the distal rotation axis Z3.

The proximal, intermediate and distal rotation axes Z1, Z2, Z3 may correspond respectively to a proximal, intermediate and distal pivot connections 11, 12, 13 of the motorized arm 20. The proximal pivot connection 11 connects the proximal end of the motorized arm 20 to the base 10. The distal pivot connection 13 connects the distal end of the motorized arm 20 to the C-arm 30.

The motorized arm 20 may comprise a proximal segment, an intermediate segment and a distal segment. The proximal segment of the motorized arm 20 is adapted to be mounted to and articulated to the mobile base 10 by means of the proximal pivot connection 11, the distal segment is adapted to be articulated to the proximal segment by means of the intermediate pivot connection 12, and the C-arm 30 is adapted to be mounted to and articulated to the distal segment of the motorized arm 20 by means of the distal pivot connection 13.

The motorized arm 20 may comprise motorization means adapted to rotate the different segments of the motorized arm 20 around the substantially vertical rotation axes Z1, Z2, Z3 relative to each other.

The translation axis Z0 in the vertical direction Z may coincide with the proximal rotation axis Z1. More specifically, the proximal pivot connection 11 may also be a slide connection, allowing both a rotation around the vertical rotation axis Z1 and a translation along the vertical rotation axis Z1. This configuration is mechanically simple. Alternatively, the translation axis Z0 in the vertical direction Z may coincide with the distal rotation axis Z3, the distal pivot connection 13 also being a slide connection.

One additional rotation axis X1, Y1 may correspond to the transverse rotation axis X1, and another additional rotation axis X1, Y1 may correspond to the C-arm rotation axis Y1.

The distal pivot connection 13 may also allow a rotation of the C-arm 30 around the C-arm rotation axis Y1 and/or the transverse rotation axis X1. Alternatively, the X-ray imaging system may comprise an additional pivot connection directed along the C-arm rotation axis Y1 and/or an additional pivot connection directed along the transverse rotation axis X1, the additional pivot connection(s) being separate from the distal pivot connection 13 and allowing a rotation around the C-arm rotation axis Y1 and/or the transverse rotation axis X1.

The distal rotation axis Z3 and/or C-arm rotation axis Y1 and/or transverse rotation axis X1 may be located at a distal end of the motorized arm 20.

More specifically, the respective pivot connection(s) corresponding to the distal rotation axis Z3 and/or C-arm rotation axis Y1 and/or transverse rotation axis X1 may be integrated in a mechanical part forming the distal end of the motorized arm 20.

Therefore, a rotation around the distal rotation axis Z3 and/or C-arm rotation axis Y1 and/or transverse rotation axis X1 only incurs a corresponding rotation of the C-arm 30, without incurring a rotation of the motorized arm 20.

Therefore, the motorized arm 20 may have significantly smaller dimensions and be significantly simpler than conventional motorized arm 20. The cost of the X-ray imaging system, as well as the room space needed to move the C-arm 30 in order to perform X-ray imaging is reduced.

In particular, when the C-arm rotation axis Y1 is located at the distal end of the motorized arm 20, the motorized arm 20 may control an orbital rotation of the C-arm 30 without incurring a corresponding rotation of the motorized arm 20 around the C-arm rotation axis Y1.

When the distal rotation axis Z3 is located at a distal end of the motorized arm 20, a rotation around the distal rotation axis Z3 incurs only a corresponding rotation of the C-arm 30 around the vertical rotation axis Z3, without incurring a rotation of the motorized arm 20 around the vertical direction Z. Such a rotation of the C-arm 30 around the distal rotation axis Z3 without incurring a rotation of the motorized arm 20 is referred to as wig-wag. Wig-wag allows the C-arm 30 to be oriented with an angle relative to the distal segment of the motorized arm 20. Wig-wag may be commanded so as to ensure that the C-arm 30 remains with a constant angle relative to the operating table throughout the displacement of the C-arm 30 in the horizontal plane H, for example remains perpendicular to the operating table.

Control Unit

The X-ray imaging system may further comprise a control unit adapted to control an actuation of the mobile base 10 and/or the motorized arm 20 and/or the C-arm.

More particularly, the control unit may be adapted to control actuation of the motorization means of the base 10 and/or motorized arm 20 and/or stabilization means 40 of the X-ray imaging system. The motorization means of the X-ray imaging system may be electric motors.

The control unit may comprise storage means, processing means such as a processor, and/or communication means.

The control unit may be integrated in the mobile base 10 of the X-ray imaging system. Alternatively, the control unit may be integrated in a separate cart. Said separate cart may comprise a user interface.

The control unit may alternatively be remote, for example may be placed in a separate control room of the hospital or in a data center.

Toppling Risk Detection Unit

The wide number of positions and orientations accessible to the C-arm 30 thanks to the movement of the motorized arm 20 leads to the center of mass of the X-ray imaging system to move significantly. Indeed, the distance between the base 10 and the C-arm 30 may undergo important variations in different directions during image acquisition.

The weights of the C-arm 30 and of the motorized arm 20 are significant. The weight of the C-arm 30 may be around 100 kg, and the weight of the motorized arm 20 may be around 100 kg.

Therefore, the displacement of the center of mass of the X-ray imaging system during image acquisition may lead to the tilting or falling of the X-ray imaging system, or the toppling of the mobile base 10.

When the motorized arm 20 is extended so as to position the C-arm 30 away from the base 10 in the transverse direction X and/or longitudinal direction Y, the center of mass is moved away from the base 10 in said transverse direction X and/or longitudinal direction Y. There is then a risk that the X-ray imaging system could topple.

More particularly, the dimension of the mobile base 10 in the longitudinal direction Y, that is to say the space separating the side wheels of the base 10, is small, as it is restricted for example by the need for the mobile base 10 to go through door frames, so as to be displaced from one room to another.

Thus, when the C-arm 30 is moved away from the base 10 both in the longitudinal and in the transverse direction X, all the more when the C-arm 30 is tilted with a given alpha angle, there is a risk that the X-ray imaging system could topple, especially around the transverse direction X.

The X-ray imaging system may further comprise a toppling risk detection unit.

The toppling risk detection unit is adapted to estimate a toppling risk of the X-ray imaging system.

Said toppling risk detection unit may be configured to continuously estimate a toppling risk of the X-ray imaging system based on encoders position of each axis of the motorized arm and a geometric model of the X-ray imaging system including a mass distribution of the X-ray imaging system.

Said mass distribution of the X-ray imaging system depends on the position and orientation of the motorized arm 20 and C-arm 30 and determines the position of the center of mass of the X-ray imaging system.

The motorized arm 20 may further be adapted to uncouple the C-arm 30 from the mobile base 10 when the toppling risk detection unit detects a toppling risk greater than a predetermined threshold. This uncoupling of the C-arm 30 may consist in a movement of the motorized arm 20 adapted to cause a progressive lowering down of the C-arm 30 until the C-arm 30 rests on the ground, the C-arm 30 thus being stabilized. Said uncoupling may be forbidden if any part of the C-arm, notably the flat panel detector, may enter in collision with the patient or another person in the operating room in the lowering movement.

The X-ray imaging system may further comprise one or more force and/or acceleration sensors adapted to detect a force and/or torque applied to the system, for example by a user. Indeed, the user may for example lean on the C-arm 30 or on the motorized arm 20, which will consequently change the center of mass of the system. The toppling risk detection unit may estimate the toppling risk of the X-ray imaging system taking into account such force and/or torque applied to the system.

Stabilization Means 40

The X-ray imaging system may further comprise stabilization means 40 adapted to stabilize the X-ray imaging system.

The stabilization means 40 are adapted to control the displacement of the center of mass of the X-ray imaging system, more particularly to keep the center of mass of the X-ray imaging system close to the mobile base in order to avoid tilting or falling of the X-ray imaging system, or toppling of the mobile base 10.

The stabilization means 40 may be mobile. More particularly, a position of the stabilization means 40 may be adapted in real time as the X-ray imaging system is moved during image acquisition or surgery, so as to counter the weight of the C-arm 30 and the motorized arm 20. The displacement of the stabilization means 40 may be calculated by the control unit by taking into account the weight of each element of the X-ray imaging system and the distance of each element relative to the base 10. The displacement of the stabilization means 40 may further take into account a force and/or torque applied to the system, for example by a user.

The stabilization means 40 may be adapted to be moved manually by an operator.

Alternatively, the stabilization means 40 may comprise motorization means adapted to automatically move the stabilization means 40. The control unit may be adapted to control said motorization means, so as to control the movement of the stabilization means 40, more particularly according to a position and orientation of the C-arm 30 and/or of the motorized arm 20.

If the stabilization means cannot be further deployed because of an obstacle, for example the operating table, the user may be warned through the user interface that the stabilization is not optimal or ensured.

The stabilization means 40 may comprise mobile counterweights. The counterweights may be integrated inside the base 10 and/or linked to the motorized arm 20. The counterweights may have a weight roughly equal to the combined weights of the C-arm 30 and the motorized arm 20. For example, for a C-arm 30 weighing around 100 kg and a motorized arm 20 weighing around 100 kg, the counterweights may for example weight around 200 kg.

The movement of the mobile counterweights may be controlled so that the more the C-arm 30 is moved away from the mobile base 10 in the transverse and/or longitudinal direction Y, the more the counterweights may be moved, oppositely to the C-arm 30, in said transverse and/or longitudinal direction Y.

Such mobile counterweights allow satisfactory stabilization of the X-ray imaging system in the transverse direction X, for most or all accessible positions and orientations of the C-arm 30. Indeed, the dimension of the mobile base 10 in the transverse direction X is sufficient to allow a significant displacement of the counterweights integrated in the base 10 along the transverse direction X, thus avoid a toppling of the X-ray imaging system around the C-arm rotation axis Y1.

Such mobile counterweights also allow satisfactory stabilization of the X-ray imaging system in the longitudinal direction Y for a certain range of positions and orientations of the C-arm 30. However, the dimension of the mobile base 10 in the longitudinal direction Y being restricted, a movement of counterweights integrated inside the mobile base 10 along the longitudinal direction Y may not be enough to stabilize the X-ray imaging system in all the positions and orientations accessible to the C-arm 30.

The stabilization means 40 may comprise retractable stabilization means 40 adapted to be moved between a retracted position and a deployed position.

In the deployed position, the stabilization means 40 provide stabilization of the X-ray imaging system. Examples of X-ray imaging systems with deployed stabilization means are illustrated in a non-limitative way in FIGS. 2b and 6a.

The deployed position may correspond to a maximum deployment state, the retracted position may correspond to a minimum deployment state. The retractable stabilization means 40 may be adapted to be moved in a number of intermediate positions between the retracted position and the deployed position, for example according to a state of extension of the motorized arm 20.

The stabilization means 40 may be implemented in alternative or in addition to the mobile counterweights in order to provide additional stabilization in any stabilization direction.

The retractable stabilization means 40 may be deployed substantially proportionally to the extension of the motorized arm 20 in the stabilization direction, that is to say to a distance between the proximal end and the distal end of the motorized arm 20 in the stabilization direction.

In the retracted position, the retractable stabilization means 40 may extend completely inside the mobile base 10. In the deployed position, the retractable stabilization means 40 may extend at least partially outwardly from the mobile base 10.

The stabilization means 40 may be deployed only when the C-arm 30 must be moved towards extreme positions away from the base 10 in the longitudinal and/or transverse directions X, Y, and/or when the C-arm 30 must be tilted with a given alpha angle. Alternatively, the stabilization means 40 may be deployed during the whole imaging procedure, or at any stage of the imaging procedure.

The retractable stabilization means 40 may be motorized so as to automatically deploy or retract according to a command of the control unit.

A displacement of the retractable stabilization means 40 between the retracted position and the deployed position may include a translation of the retractable stabilization means 40 along the stabilization direction.

Said translation may be substantially proportional to a distance between the proximal end and the distal end of the motorized arm 20 in the stabilization direction.

In a first embodiment, the retractable stabilization means 40 include two balance weights. A distance separating the two balance weights is greater in the deployed position than in the retracted position. The two balance weights may extend close to or on the ground, in both the deployed and the retracted positions.

The two balance weights may be mounted on the two sides of the mobile base 10.

The stabilization direction may correspond to the longitudinal direction Y.

The two balance weights may be disposed at respective ends of two retractable stabilizing feet mounted on the mobile base 10.

In a first example, each of the two balance weights is fixed to a respective side of the base 10 by a respective pivot connection directed along the vertical direction Z. Each pivot connection allows rotation of the respective balance weight around the vertical direction Z. The balance weight may be rotated by substantially 90° around the vertical direction Z between the retracted position and the deployed position.

In the retracted position, each balance weight may be positioned against the side of the mobile base 10 on which it is mounted, and may extend substantially in the transverse direction X. The retracted position allows a lesser footprint of the base 10 on the ground, and may be used for transport of the X-ray imaging system. In particular, the footprint of the base 10 in the longitudinal direction Y when the stabilization means 40 are retracted is the same as the footprint of a base 10 without said retractable stabilization means 40. Therefore, the stabilization is performed without increasing the footprint of the base 10.

In the deployed position, the balance weights may be positioned substantially perpendicularly to the side of the mobile base 10 on which it is mounted, and may extend substantially in the longitudinal direction Y. Each balance weight may extend at least partially outside the base 10, an end of the balance weight extending in the base 10 and another end of the balance weight extending away from the base 10 in the longitudinal direction Y. The deployed position allows a maximum dimension of the base 10 in the longitudinal direction Y, thus stabilizing the X-ray imaging system in the longitudinal direction Y.

In a second example, each of the two balance weights may be retracted or deployed by a translation in a longitudinal direction Y, in a longitudinal direction Y, and/or in diagonal direction between the longitudinal direction Y and the transverse direction X. For example, each of the two balance weights may be retracted or deployed by a translation in a direction oriented at substantially 45° from the longitudinal direction Y and the transverse direction X, as illustrated example in FIGS. 2b and 6a.

The stabilization direction of a first balance weight located on a first side of the base 10 may be symmetrical relative to an axis oriented in the traverse direction X and passing through a center of the base 10 to the stabilization direction of a second balance weight located on a second opposite side of the base 10.

In a second embodiment, the retractable stabilization means 40 include at least one retractable suction pad. The at least one retractable suction pad is adapted to adhere to the ground in the deployed position.

More specifically, each suction pad may extend substantially in the vertical direction Z. In the retracted position, the suction pad may be partially or integrally retracted inside the base 10. The suction pad may be moved towards the deployed position by a downward vertical translation, and may reach the deployed position when the suction pad contacts the ground. Suction by the suction pad may be activated for example by a motor such as an electric motor, or by a pump.

Several suction pads may be arranged at different locations relative to the base 10, so as to maximize the suction provided by the suction pads and thus the corresponding stabilization of the X-ray imaging system.

Alerting Means

The X-ray imaging system may further comprise alerting means adapted to alert an operator to move the stabilization means 40 when the toppling risk detection unit detects a toppling risk. The alert may for example be a visual and/or an audible alert.

Thus, the user is alerted as to the need of using stabilization means 40 according to a configuration of the X-ray imaging system.

In alternative, the alerting means may be adapted to alert the control unit to move the stabilization means 40 when the toppling risk detection unit detects a toppling risk, so that the control unit may automatically move the stabilization means 40 accordingly.

Authorized Area of Motion

The toppling risk detection unit may be adapted to determine an authorized area of motion of the C-arm 30 according to toppling parameters.

The control unit is adapted to restrict a movement of the motorized arm 20 so as to keep the C-arm 30 within said determined authorized area of motion.

The control unit thus allows movement of the motorized arm 20 when the C-arm 30 remains within the determined authorized area of motion, and restricts movement of the motorized arm 20 which would lead the C-arm 30 to be positioned outside said determined authorized area of motion.

The determined authorized area of motion may correspond to an area for the C-arm 30 wherein the overall balance of the X-ray imaging system, that is to say the stability of the X-ray imaging system, is ensured. Thus, the X-ray imaging system cannot move to positions and orientations where the weight distribution would be inappropriate and risk toppling of the X-ray imaging system.

Alternatively, the control unit may allow movement of the motorized arm 20 which correspond to the C-arm 30 being positioned either inside or outside the authorized area of motion, but generate an alert when the C-arm 30 is located outside said authorized area of motion. Therefore, the user is alerted as to a potential risk concerning the stability of the X-ray imaging system.

The authorized area may be determined in real time during the imaging procedure, according to a movement of the mobile base 10 and/or the motorized arm 20.

The authorized area of motion may be an area defined relative to the base 10. Some positions of the C-arm 30 are thus forbidden, so that the C-arm 30 is not moved in positions too far away from the base 10. Alternatively, the authorized area of motion may be an area defined relative to the center of mass of the X-ray imaging system, so as to keep said center of mass in an area which does not generate a toppling risk of the X-ray imaging system.

The authorized area of motion may correspond to at least one authorized rotation limit on at least one of the at least three rotation axes Z1, Z2, Z3 of the motorized arm 20.

The toppling parameters used by the toppling risk detection unit in order to determine the authorized area of motion may comprise a weight and/or a position of the motorized arm 20, the C-arm 30, and/or the base 10. The toppling parameters may include force and/or torque applied to the system.

If the X-ray imaging system comprises stabilization means 40, the toppling parameters used by the toppling risk detection unit in order to determine the authorized area of motion may include operating parameters of the stabilization means 40.

Such operating parameters of the stabilization means 40 may include a weight and/or a position of the stabilization means 40, and/or may reflect a configuration of the stabilization means 40.

For example, the authorized area may be wider when the stabilization means 40 are in the deployed position, than when the stabilization means 40 are in the retracted position. Indeed, the range of positions and orientations of the C-arm 30 without compromising the stability of the system is wider when the stabilization means 40 are deployed.

User Interface

The X-ray imaging system may further comprise a user interface adapted to allow a user to control a movement of the mobile base 10 and/or the motorized arm 20.

The user interface may also be adapted to control an X-ray acquisition by the C-arm 30.

The user interface may comprise switches, such as a power switch adapted to begin or stop an image acquisition by the C-arm 30, an emergency button adapted to stop a movement of the motorized arm 20 and/or the C-arm 30, etc.

The user interface may be integrated in the base 10, more particularly may be positioned on an external face of the base 10, so as to be visible by a user positioned near the base 10.

Alternatively, the user interface may be remote from the base 10. For example, the user interface may be displayed on a screen of a computer distant from the base 10, the screen comprising virtual buttons allowing a user to control actuation of the motorized arm 20. Alternatively, the user interface may be duplicated remotely to allow remote control.

Cooperative Mode

The X-ray imaging system may further comprise a sensor adapted to measure a force and/or torque applied by a user on the motorized arm 20 and/or the C-arm 30.

The control unit may comprise a cooperative mode. In the cooperative mode, the control unit is adapted to control a movement of the motorized arm 20 in response to the force and/or torque detected by the sensor.

The cooperative mode may be parameterized so that:
 when the sensor detects a force and/or torque in one or several direction(s), the control unit applies a substantially proportional force and/or torque to the motorized arm 20, and
 when the sensor detects a force and/or torque in one or several other direction(s), the control unit does not apply a force and/or torque to the motorized arm 20.

Thus, in the cooperative mode, the movement of the motorized arm 20, thus of the C-arm 30, may be controlled, or driven, by a user directly manipulating the C-arm 30 or the motorized arm 20. A user action on the X-ray imaging system may lead to a corresponding C-arm 30 movement only in some directions, so as to give the user some freedom on the positioning of the C-arm 30 while maintaining a satisfactory precision in said positioning of the C-arm 30.

For example, the control unit may apply a substantially proportional force and/or torque to the motorized arm 20 to the force and/or torque detected in the horizontal plane H, but not to the force and/or torque detected in the vertical direction Z. Thus, the user may not change the vertical position of the C-arm 30 by applying a force and/or torque on the X-ray imaging system. Alternatively, the collaborative mode may be parameterized so that a user action on the X-ray imaging system may only lead to move the C-arm 30 in the vertical direction Z. Thus, the rest of the positioning and orientating of the C-arm 30 is automatically managed by the control unit.

Alternatively, the control unit may apply a substantially proportional force and/or torque to the motorized arm 20 to the force and/or torque applied by a user on the C-arm 30 in order to modify the alpha angle of the C-arm 30, but not in any other directions.

The cooperative mode may be activated or deactivated by a user, for example by pressing a corresponding button on the X-ray imaging system, or by selecting a corresponding option on the user interface.

Parking Configuration

The X-ray imaging system may be adapted to be actuated towards a parking configuration optimized to reduce a footprint of said X-ray imaging system. The parking configuration is optimized for storage, whether inside or outside the operating room, and/or for transport.

The parking configuration may consist in a specific position and orientation of the motorized arm 20 and C-arm 30 so as to reduce the footprint of the X-ray imaging system and minimize the risk of collision of any critical part of the X-ray imaging system with the environment when displaced (walls, doors etc.). Furthermore, in the parking configuration, the X-ray imaging system may be stabilized so as to minimize or eliminate the toppling risk.

The mobile base 10 may be present an external surface adapted for such parking configuration. More particularly, an external surface of the mobile base 10 may be complementary in shape to the C-arm 30. The external surface of the mobile base may be curved with a radius of curvature corresponding substantially to a radius of curvature of the C-shaped structure, or the O-shaped structure, of the C-arm 30.

In the parking configuration, the C-arm 30 may lie at least partially on the external surface of the mobile base 10. More specifically, the C-shaped structure, or the O-shaped structure, of the C-arm 30 may rest on the mobile base 10, so that the mobile base 10 at least partially supports a weight of the X-ray imaging system. This allows a greater mechanical rest of the motorized arm 20. Especially during transportation, as the mobile base 10 may be displaced on uneven ground, it is the mobile base 10 which then absorbs the resulting vibrations of the X-ray imaging system, instead of the motorized arm 20, thus preserving the motorized arm 20. Examples corresponding to an embodiment in which the C-arm 30 lies on the mobile base 10 are illustrated in FIGS. 3a to 3c, and 5b.

The X-ray imaging system may be placed in the parking configuration by automatic and synchronized actuations of the motorized arm 20 and C-arm 30, for example in response to the pressing of a button by the user at the end of surgery.

Symmetrical or Asymmetrical Architecture of the X-Ray Imaging System

The X-ray imaging system may present an asymmetrical architecture. More specifically, the motorized arm 20 may be mounted off-center relative to a plane of symmetry of the mobile base 10. The plane of symmetry of the mobile base 10 may be oriented in the vertical direction Z and in the transverse direction X, and may pass substantially through a center of an external surface of the mobile base 10. For example, the proximal pivot connection 11 may be positioned off-center relative to the plane of symmetry of the mobile base 10, the mobile arm 20 being mounted to the mobile base 10 by way of the proximal pivot connection 11. Examples of X-ray imaging systems with an asymmetrical architecture are illustrated, in a non-limitative way, in FIGS. 1, 2a to 3c, 5a and 5b.

Such an asymmetrical architecture of the X-ray imaging system may not result in an asymmetrical area of motion of the C-arm 30, as the off-center positioning of the motorized arm 20 may be compensated by an adequate management of mechanical abutments and configuration of the control unit.

The asymmetrical architecture may allow an optimization of the footprint of the X-ray imaging system when the X-ray imaging system is in the parking configuration. More specifically, in the parking configuration, the C-arm 30 may entirely lie within the footprint of the mobile base 10. Thus, the sensitive parts of the C-arm 30, in particular the X-ray source 31 and the X-ray detector 32, are protected from collision with adjacent elements. Examples of X-ray imaging systems with an asymmetrical architecture, the X-ray imaging systems being in the parking configuration are illustrated, in a non-limitative way, in FIGS. 3a to 3c and 5b.

Alternatively, the X-ray imaging system may present a symmetrical architecture. More specifically, the motorized arm 20 may be mounted substantially at the plane of symmetry of the mobile base 10. Thus, the authorized area of motion of the C-arm 30 is symmetrical relative to the mobile base 10. Examples of X-ray imaging systems with a symmetrical architecture are illustrated, in a non-limitative way, in FIGS. 4a, 4b, 6a and 6b.

Figure 4A:
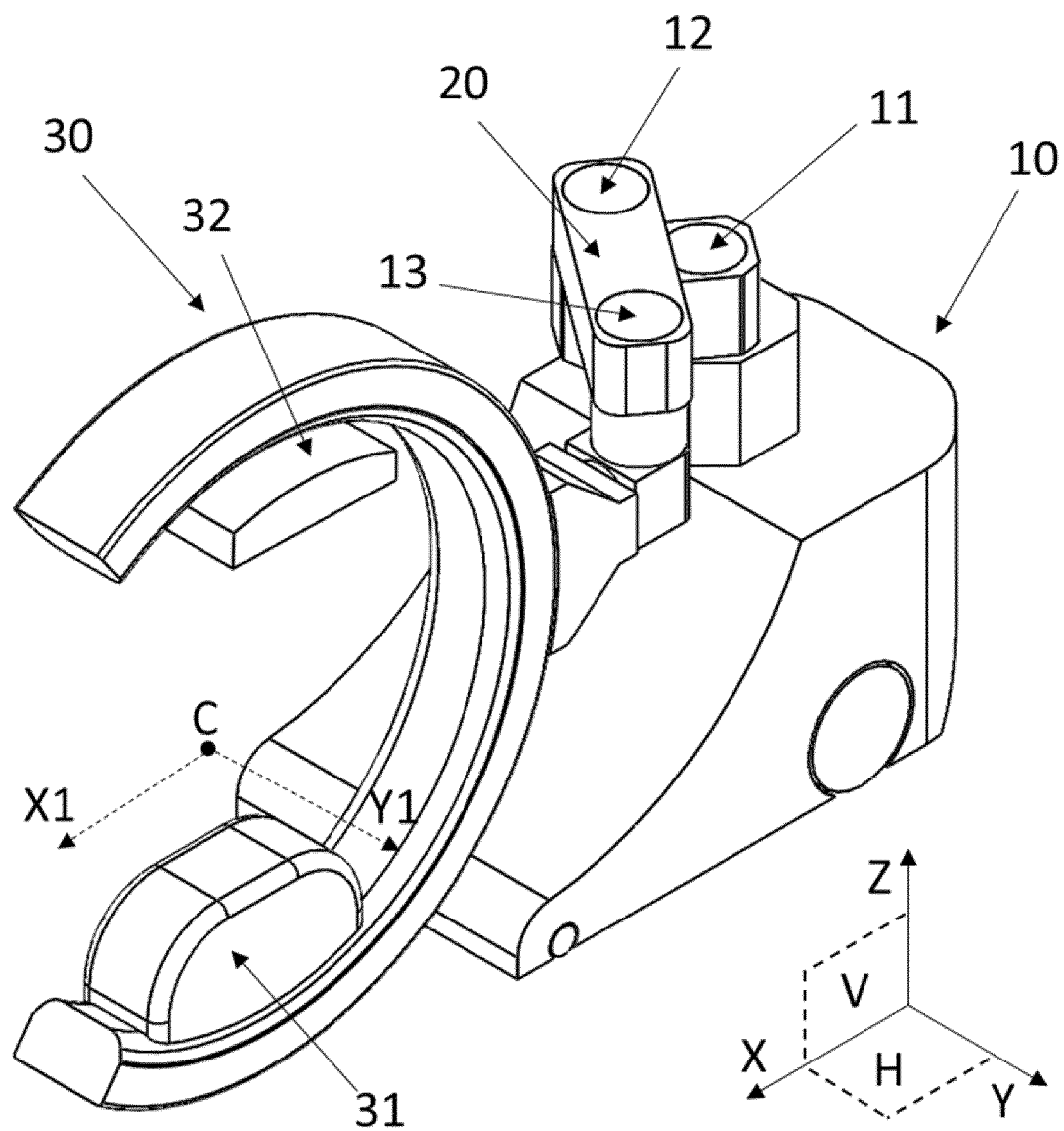
FIG. 4a is a perspective view of an X-ray imaging system according to an embodiment of the invention, the X-ray imaging system having a symmetrical architecture.
Figure 4B:
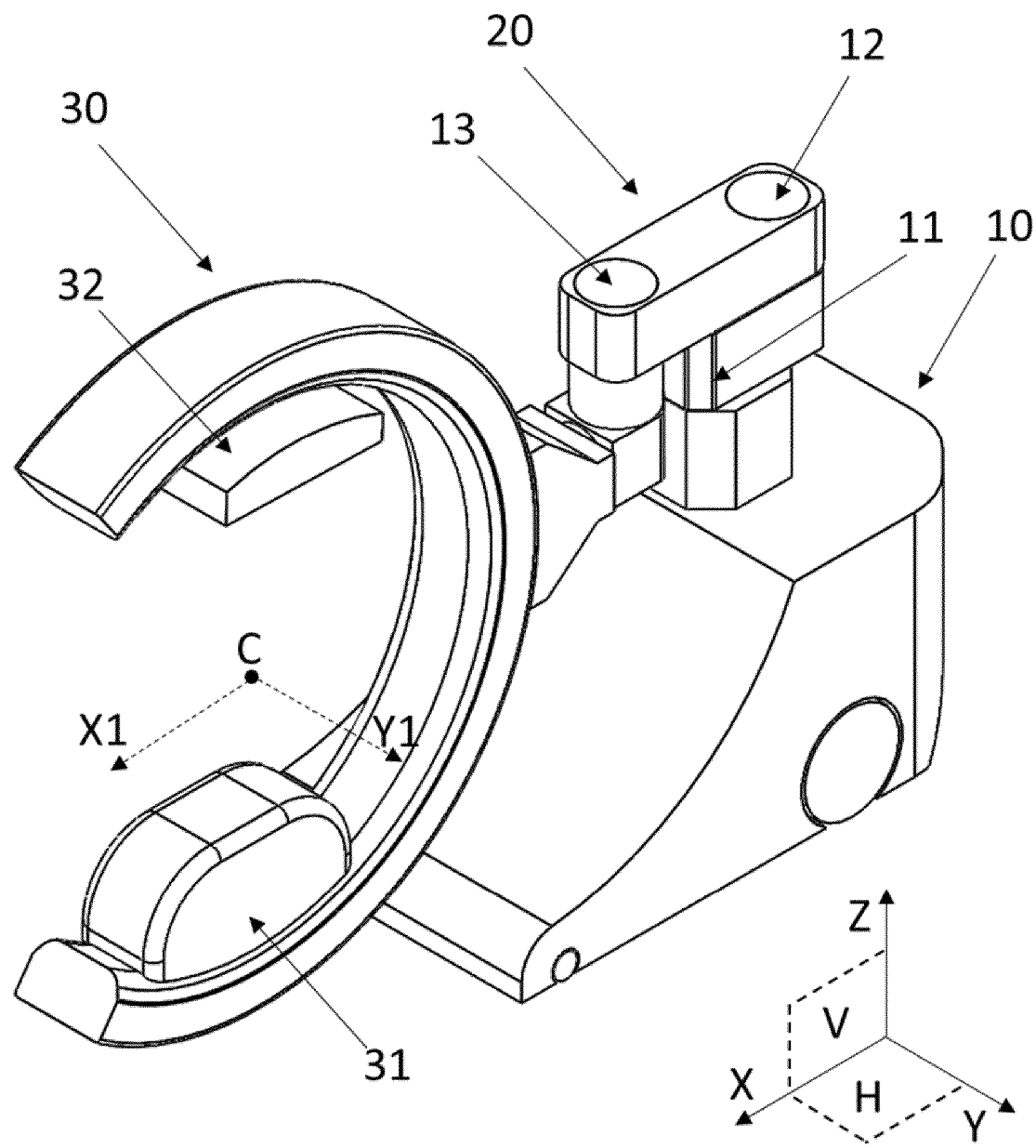
FIG. 4b is a perspective view of the X-ray imaging system illustrated in FIG. 4a, the X-ray imaging system being in the parking configuration.
Figure 5A:
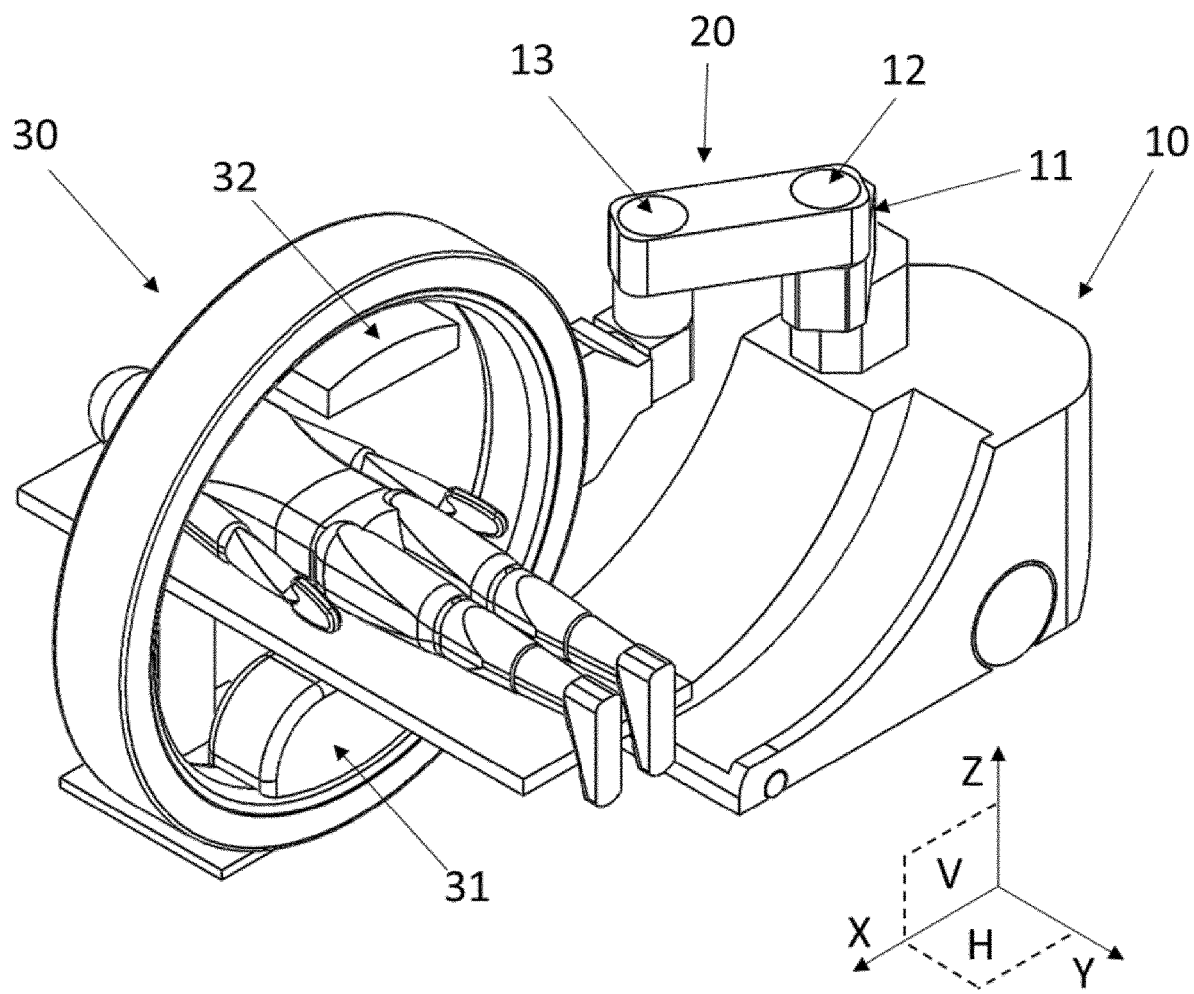
FIG. 5a is a perspective view of an X-ray imaging system according to an embodiment of the invention, the X-ray imaging system having a C-arm with an O-shaped structure.
Figure 5B:
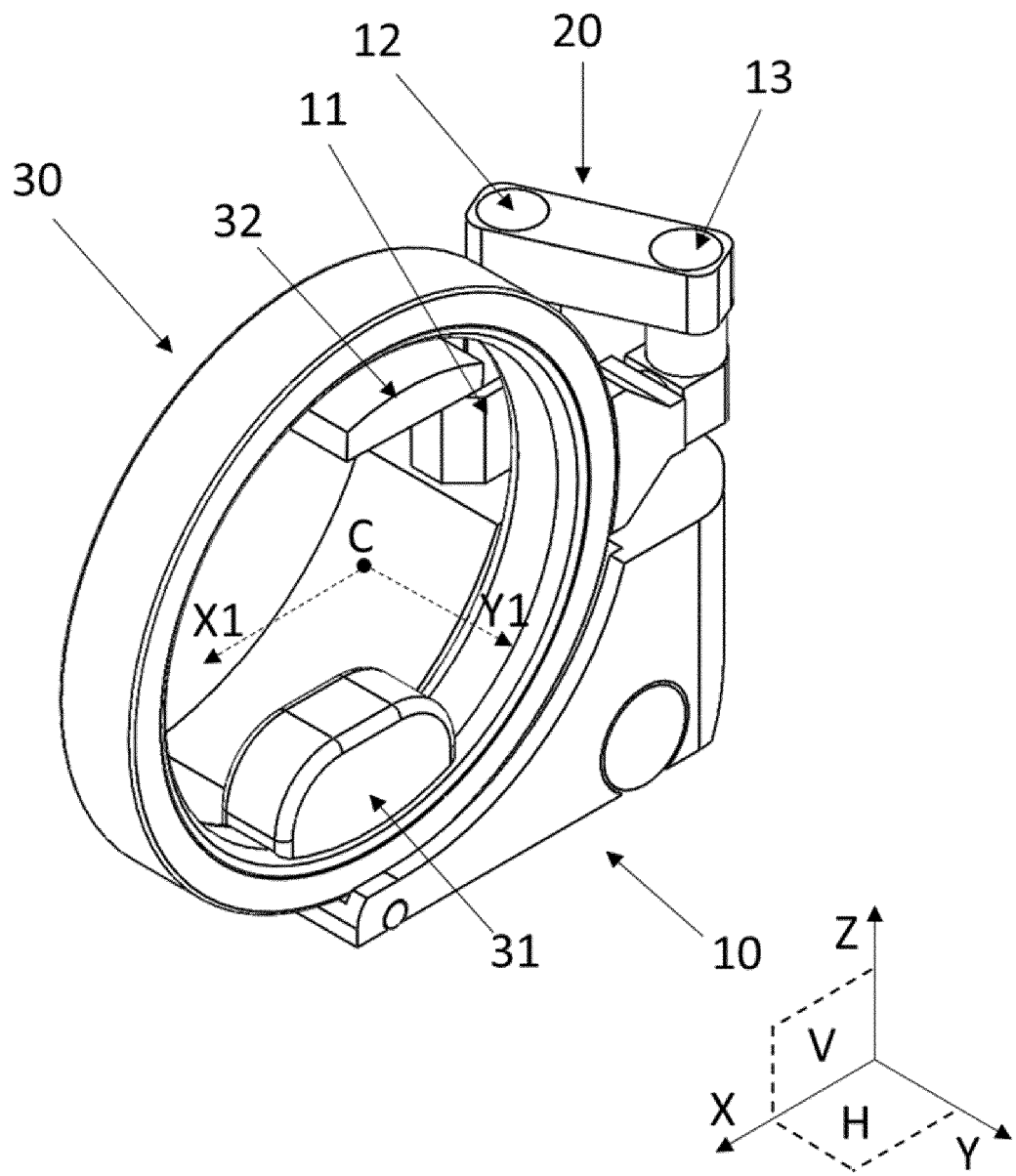
FIG. 5b is a perspective view of the X-ray imaging system illustrated in FIG. 5a, the X-ray imaging system being in the parking configuration.
Figure 6B:
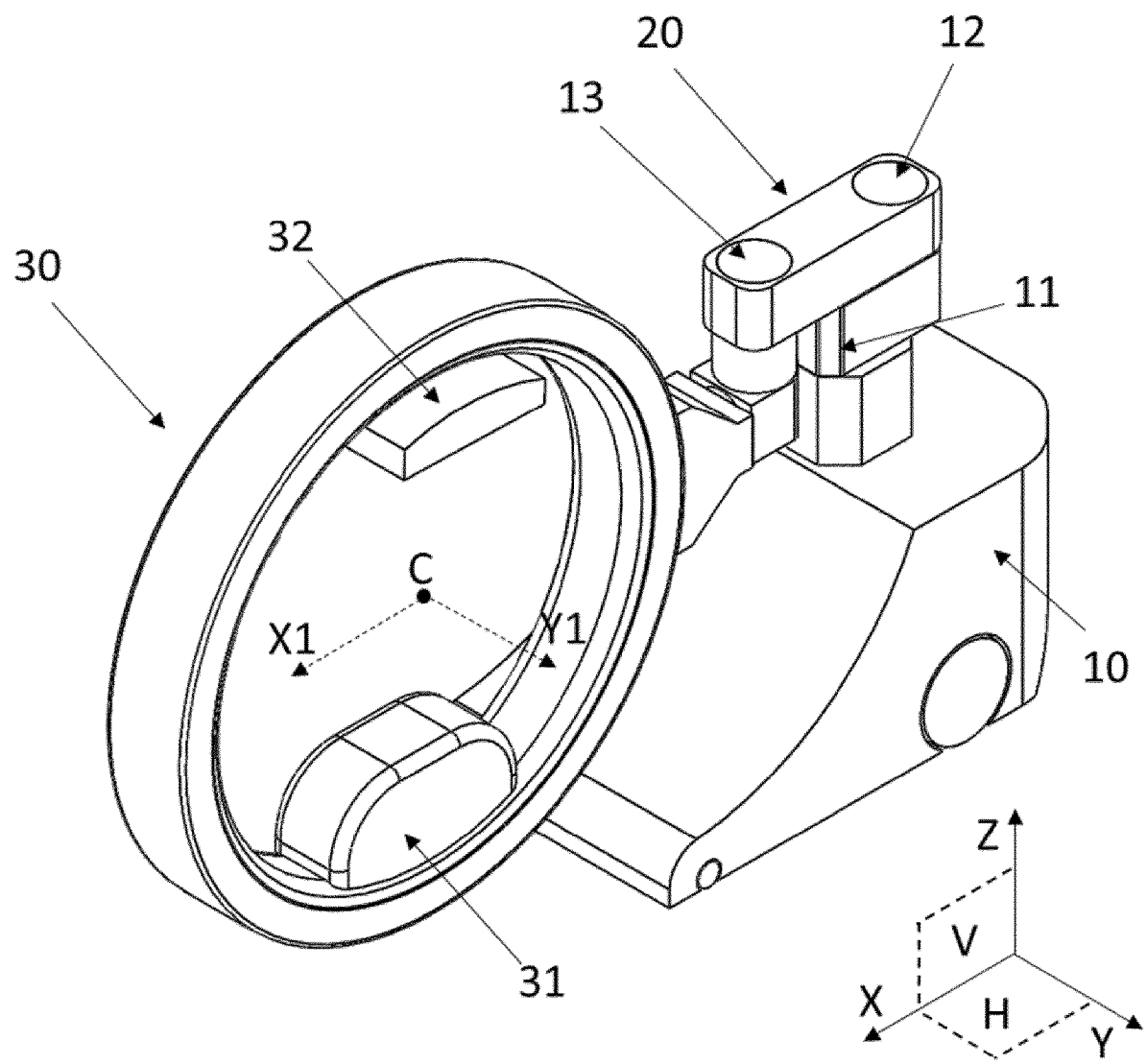
FIG. 6b is a perspective view of the X-ray imaging system illustrated in FIG. 6a, the X-ray imaging system being in the parking configuration, with retracted stabilization means.

Parking positions of X-ray imaging systems presenting a symmetrical architecture is represented by way of a non-limiting example, in FIGS. 4b and 6b.

Battery-Powered Supply Unit

The X-ray imaging system may further comprise a battery-powered supply unit for safe operation in the case of a power outage.

The battery-powered supply unit may be dimensioned so as the X-ray imaging system can return to the parking configuration on said battery. More specifically, the battery may be dimensioned so as to supply power to actuate the mobile arm 20 and/or the C-arm 30 in order to place the X-ray imaging system back into the parking configuration, independently of the previous configuration, in terms of position of the C-arm 30 and mobile arm 20, of the X-ray imaging system.

The battery may be integrated in the mobile base 10.

Thus, in the case of a power outage, the battery may place the X-ray imaging system in the parking configuration. The X-ray imaging system thus does not risk falling on the patient, and may then be easily transported outside the operation room, so that it is not susceptible to represent any risk for the patient.

General Presentation of a Method for Acquiring an Imaging Dataset

A method for acquiring an imaging dataset with an X-ray imaging system according to any of the embodiments disclosed above comprises the following steps:

S1: controlling a movement of the mobile base 10 and/or the motorized arm 20 in order to position the C-arm 30 relative to a predetermined region of interest;

S2: acquiring an imaging dataset of the predetermined region of interest by the X-ray imaging system.

This method allows to acquire imaging dataset by an X-ray imaging system comprising a simple single motorized arm 20. The movement of the motorized arm 20 and mobile base 10 may be controlled accurately so as to position the C-arm 30 in a wide range of positions in directions relative of the predetermined region of interest, with a high level of precision.

The method thus makes it possible to successively acquire distant imaging datasets of distant regions of interest, by moving the C-arm 30 between the successive acquisitions, while knowing that the movement command has been respected. Therefore, the position of the C-arm 30 does not have to be recalibrated in a specific recalibration step for each region of interest acquired.

The C-arm 30 is positioned relative to a predetermined region of interest. That is to say, the C-arm 30 is positioned so as to be able to begin acquisition of the predetermined region of interest, at least a part of the region of interest being positioned between the X-ray source 31 and the X-ray detector 32. The base 10 may be positioned along the operating table on which the person lies, at a distance from the operating table.

Acquisition of Several Regions of Interest

The method may comprise the following steps, performed successively for at least one additional region(s) of interest, after acquiring the imaging dataset of the predetermined region of interest in step S2:

S3: controlling a movement of the mobile base 10 and/or the motorized arm 20 in order to position the C-arm 30 relative to an additional region of interest;

S4: estimating a displacement of the motorized arm 20 corresponding to the movement controlled in step S3 by a motorized arm 20 kinematic model;

S5: acquiring an additional imaging dataset of the additional region of interest by the X-ray imaging system;

S6: estimating a displacement of the X-ray detector 32 of the C-arm 30 between the acquisition of the previous region of interest and the additional region of interest base 10d on the displacement of the motorized arm 20 estimated in step S4.

This method allows the acquisition of at least two imaging datasets, corresponding to at least two regions of interest (at least the predetermined region of interest, and at least one additional region of interest).

The at least two imaging datasets may be geometrically registered together by using the motorized arm 20 kinematic model. Indeed, the C-arm 30 displacement throughout the process, in particular between two imaging acquisitions, may be accurately tracked, as the commanded motorized arm 20 movement corresponds to the actual observed motorized arm 20 movement.

Therefore, a position of the C-arm 30 relative to an additional region of interest may be deduced from a reference position of the C-arm 30 relative to the predetermined region of interest and from the estimated displacement of the motorized arm 20.

The steps S3, S4, S5 and S6 may be repeated successively for at least two additional regions of interest.

In one example, the predetermined region of interest is a knee of a person, a first additional region of interest is a hip of the person, and a second additional region of interest is an ankle of the person. A first imaging dataset may be a 3D image of the knee, a second imaging dataset may comprise at least two 3D projections of the hip, and a third imaging dataset may comprise at least two 2D projections of the ankle of the person.

In another example, at least two regions of interest among the predetermined region of interest and the at least one additional region(s) of interest are two different sections of a spine of a person. These regions of interest may correspond to imaging acquisitions during a procedure performed on a person having scoliosis, and allows tracking the way the spine is repositioned during surgery.

Calibration of a Position of the C-Arm 30 Relative to a Reference Tracker

The method may further comprise performing the following steps before each acquisition of an imaging dataset of a region of interest:

S11: positioning a reference tracker in a fixed relation relative to the region of interest to acquire;

S12: estimating a position of the X-ray detector 32 of the C-arm 30 relative to the reference tracker.

The method further comprises a step S7 of registering the at least one additional region(s) of interest with the predetermined region of interest based 10 on the displacement of the motorized arm 20 estimated in step S4.

The reference tracker may be a calibration marker such as a radiopaque fiducial.

The reference tracker is positioned on the person, in a known position relative to the region of interest to acquire. The reference tracker may be fixed onto the person.

The C-arm 30 may be positioned roughly on the reference tracker, either manually by a user, or automatically by the control unit. The C-arm 30 then acquires an image or an imaging dataset.

The reference tracker is thus visible in at least one acquired image of each of the imaging datasets acquired by the X-ray imaging system, or a subset of the acquired imaging dataset. The position of the C-arm 30 may thus be determined from the position of the reference tracker in the acquired image. More particularly, the position of the X-ray detector 32 relative to the person and the relative positions of the X-ray detector 32 between the different image acquisitions are therefore known. The position of the C-arm 30 may correspondingly be adjusted.

Synchronized Base 10 and Motorized Arm 20 Movement

The method may further comprise the following steps, performed substantially simultaneously:

S7: moving the mobile base 10;

S8: determining a displacement of the mobile base 10 by a base position sensor;

S9: synchronizing a movement of the motorized arm 20 with the displacement of the mobile base 10 determined in step S8 by base motorization means, so that a position of the C-arm 30 remains substantially the same.

The control unit may be adapted to synchronize the movement of the motorized arm 20 with the displacement of the mobile base 10, when the base position sensors detect a movement of the base 10. The control unit may command an automatic movement of the base 10 via the base motorization means.

The mobile base 10 and the motorized arm 20 are moved in a synchronized manner, so as to maintain the C-arm 30 in a fixed position relative to the region of interest to be imaged. The movement of the motorized arm 20 compensates in real time the movement of the base 10.

Therefore, when the mobile base 10 is moved, for example by a user, the C-arm 30 remains at substantially the same position with respect to the region of interest to acquire and may go on with the image acquisition without interrupting the image acquisition.

Therefore, the mobile base 10 may be moved during surgery or even during image acquisition, while the C-arm 30 remains in a stable position relative to the region of interest to be imaged.

More particularly, the base 10 may be translated in the horizontal plane H along the longitudinal direction Y and/or along the transverse direction X, while maintaining the C-arm 30 in a fixed position thanks to a synchronized counter-movement of the motorized arm 20.

For example, if the user wants to free up space where the base 10 is located, the user can move the base 10 without causing movement of the C-arm 30.

Coordinated Control of the Motorized Arm 20

The method may further comprise a step S110 of controlling, in a coordinated manner, a movement of the motorized arm 20 around at least two of the at least three rotation axes Z1, Z2, Z3, so as to move the C-arm 30 in a substantially horizontal plane H attached to the mobile base 10.

This step allows moving the C-arm 30 without causing any variation of the position along the vertical direction Z, or any variation of the alpha angle of the C-arm 30.

The method may further comprise a step S120 of controlling, in a coordinated manner, a movement of the motorized arm 20 around at least two of the at least three rotation axes Z1, Z2, Z3, so as to move the C-arm 30 around a fixed point or a fixed axis.

The fixed point or fixed axis may be located substantially at an isocenter C of the C-arm 30, at a substantially equal distance from the X-ray source 31 and the X-ray detector 32.

The C-arm 30 thus remains on the fixed point or axis, while its position and/or orientation, for example its alpha angle or wig-wag, is moved. For example, the C-arm 30 may be positioned on a vertebra and then be maintained in a fixed position relative to the vertebra while its alpha angle and/or wig-wag is modified. Alternatively, the C-arm 30 may be positioned on a vertebra and then the motorized arm 20 may be manually moved so as to align the C-arm 30 relative to the vertebral plates, while maintaining a center of the C-arm 30 in a fixed position.

Position Storage

The method may further comprise a step S130 of memorizing, by a control unit, at least one position of the C-arm 30 along with corresponding position parameters of the motorized arm 20.

The position parameters of the motorized arm 20 may be representative of an extension of the motorized arm 20, thus of a position of the C-arm 30. For example, the position parameters may comprise angular values of a state of angular rotation of the different segments of the motorized arm 20 around each of the rotation axes X1, X2, X3.

The method may further comprise a step S140 of controlling a movement of the motorized arm 20 in order to position the C-arm 30 to a position memorized by the control unit.

Therefore, a user performing the imaging may command the motorized arm 20 to automatically go back and forth between several memorized imaging positions.

Other embodiments can be envisaged and a person skilled in the art can easily modify the embodiments or examples of realization exposed above or envisage others while remaining within the scope of the invention.

The invention claimed is:

1. An X-ray imaging system comprising a mobile base, a motorized arm, a C-arm adapted to be mounted on the mobile base by means of the motorized arm and a control unit adapted to control an actuation of the mobile base and/or the motorized arm,
   wherein the C-arm comprises an X-ray source and an X-ray detector,
   wherein the motorized arm presents at least three rotation axes directed along a substantially common vertical direction,
   wherein the X-ray imaging system further comprises a sensor adapted to measure a force and/or torque applied by a user on the motorized arm and/or the C-arm, wherein the control unit comprises a cooperative mode, wherein in the cooperative mode, the control unit is adapted to control a movement of the motorized arm in response to the force and/or torque detected by the sensor.

2. The X-ray imaging system according to claim 1, wherein the motorized arm further presents a translation axis in the vertical direction.

3. The X-ray imaging system according to claim 1, wherein the motorized arm further presents at least one additional rotation axis.

4. The X-ray imaging system according to claim 1, wherein the motorized arm presents a kinematic chain of six axes, starting from the mobile base and comprising successively:
   a translation axis along the vertical direction,
   three successive rotation axes parallel to the vertical direction,
   a transverse rotation axis substantially orthogonal to the vertical direction,
   a C-arm rotation axis substantially orthogonal to the vertical direction and to the transverse rotation axis.

5. The X-ray imaging system according to claim 1, further comprising a toppling risk detection unit adapted to estimate a toppling risk of the X-ray imaging system.

6. The X-ray imaging system according to claim 5, wherein the toppling risk detection unit is configured to continuously estimate a toppling risk of the X-ray imaging system based on encoders position of each axis of the motorized arm and a geometric model of the X-ray imaging system including a mass distribution of the X-ray imaging system.

7. The X-ray imaging system according to claim 1, wherein the mobile base comprises motors adapted to move the mobile base in a substantially horizontal plane and a base position sensor adapted to determine a position of the mobile base in said horizontal plane.

8. The X-ray imaging system according to claim 5, further comprising a control unit adapted to control an actuation of the mobile base and/or the motorized arm, wherein the toppling risk detection unit is adapted to determine an authorized area of motion of the C-arm according to toppling parameters, and wherein the control unit is adapted to restrict a movement of the motorized arm so as to keep the C-arm within said determined authorized area of motion.

9. The X-ray imaging system according to claim 1, wherein said cooperative mode is parameterized so that:
   when the sensor detects a force and/or torque in one or several direction(s), the control unit applies a substantially proportional force and/or torque to the motorized arm (20), and
   when the sensor detects a force and/or torque in one or several other direction(s), the control unit does not apply a force and/or torque to the motorized arm (20).

10. A method for acquiring an imaging dataset with an X-ray imaging system according to claim 1, comprising the following steps:
    S1: controlling, by a control unit of the X-ray imaging system, a movement of a mobile base and/or a motorized arm of the X-ray imaging system in order to position a C-arm of the X-ray imaging system relative to a predetermined region of interest, wherein the C-arm is adapted to be mounted on the mobile base by means of the motorized arm, wherein the C-arm comprises an X-ray source and an X-ray detector, wherein the motorized arm presents at least three rotation axes directed along a substantially common vertical direction;

S2: acquiring an imaging dataset of the predetermined region of interest by the X-ray imaging system;

measuring a force and/or torque applied by a user on the motorized arm and/or the C-arm by a sensor; and when the control unit is in a cooperative mode, controlling, by the control unit, a movement of the motorized arm in response to the force and/or torque detected by the sensor.

11. The method for acquiring an imaging dataset according to claim 10, further comprising the following steps, performed successively for at least one additional region of interest, after acquiring the imaging dataset of the predetermined region of interest in step S2:

S3: controlling a movement of at least one of the mobile base and the motorized arm in order to position the C-arm relative to an additional region of interest;

S4: estimating a displacement of the motorized arm corresponding to the movement controlled in step S3 by a motorized arm kinematic model;

S5: acquiring an additional imaging dataset of the additional region of interest by the X-ray imaging system;

S6: estimating a displacement of the X-ray detector of the C-arm between the acquisition of the previous region of interest and the additional region of interest based on the displacement of the motorized arm estimated in step S4.

12. The method for acquiring an imaging dataset according to claim 11, wherein the method further comprises performing the following steps before each acquisition of an imaging dataset of a region of interest:

S11: positioning a reference tracker in a fixed relation relative to the region of interest to acquire;

S12: estimating a position of the X-ray detector of the C-arm relative to the reference tracker;

and wherein the method further comprises a step S7 of registering the at least one additional region of interest with the predetermined region of interest based on the displacement of the motorized arm estimated in step S4.

13. The method for acquiring an imaging dataset according to claim 10, further comprising the following steps, performed substantially simultaneously:

S7: moving the mobile base;

S8: determining a displacement of the mobile base by a base position sensor;

S9: synchronizing a movement of the motorized arm with the displacement of the mobile base determined in step S8 by base motors, so that a position of the C-arm remains substantially the same.

14. The method according to claim 10, further comprising a step S110 of controlling, in a coordinated manner, a movement of the motorized arm around at least two of the at least three rotation axes, so as to move the C-arm in a substantially horizontal plane attached to the mobile base.

15. The method according to claim 10, further comprising a step S120 of controlling, in a coordinated manner, a movement of the motorized arm around at least two of the at least three rotation axes, so as to move the C-arm around a fixed point or a fixed axis.

16. The method according to claim 15, wherein the fixed point or fixed axis is located substantially at an isocenter of the C-arm, at a substantially equal distance from the X-ray source and the X-ray detector.

17. The method according to claim 10, further comprising a step S130 of memorizing, by a control unit, at least one position of the C-arm along with corresponding position parameters of the motorized arm.

18. The method according to claim 17, further comprising a step S140 of controlling a movement of the motorized arm in order to position the C-arm to a position memorized by the control unit.

19. An X-ray imaging system comprising a mobile base, a motorized arm, and a C-arm adapted to be mounted on the mobile base by means of the motorized arm, wherein the C-arm comprises an X-ray source and an X-ray detector, wherein the motorized arm presents at least three rotation axes directed along a substantially common vertical direction, wherein the X-ray imaging system further comprises a toppling risk detection unit configured to continuously estimate a toppling risk of the X-ray imaging system, wherein the toppling risk detection unit is configured to continuously estimate a toppling risk of the X-ray imaging system based on encoders position of each axis of the motorized arm and a geometric model of the X-ray imaging system including a mass distribution of the X-ray imaging system.

* * * * *